United States Patent
Mizuno et al.

(10) Patent No.: US 10,280,223 B2
(45) Date of Patent: May 7, 2019

(54) ANTI-CANINE PD-1 ANTIBODY OR ANTI-CANINE PD-L1 ANTIBODY

(71) Applicant: NIPPON ZENYAKU KOGYO CO., LTD., Fukushima (JP)

(72) Inventors: Takuya Mizuno, Yamaguchi (JP); Kazuha Shosu, Yamaguchi (JP)

(73) Assignee: NIPPON ZENYAKU KOGYO CO., LTD., Fukushima (JP)

( * ) Notice: Subject to any disclaimer, the term of this patent is extended or adjusted under 35 U.S.C. 154(b) by 303 days.

(21) Appl. No.: 15/320,412

(22) PCT Filed: Jul. 8, 2015

(86) PCT No.: PCT/JP2015/003444
§ 371 (c)(1),
(2) Date: Dec. 20, 2016

(87) PCT Pub. No.: WO2016/006241
PCT Pub. Date: Jan. 14, 2016

(65) Prior Publication Data
US 2017/0158764 A1 Jun. 8, 2017

(30) Foreign Application Priority Data
Jul. 9, 2014 (JP) ................. 2014-140982

(51) Int. Cl.
*C07K 16/28* (2006.01)
*A61K 39/395* (2006.01)
*C12N 15/09* (2006.01)

(52) U.S. Cl.
CPC ........ *C07K 16/2803* (2013.01); *A61K 39/395* (2013.01); *C07K 16/2818* (2013.01); *C07K 16/2827* (2013.01); *C12N 15/09* (2013.01); *C07K 2317/20* (2013.01); *C07K 2317/34* (2013.01); *C07K 2317/76* (2013.01)

(58) Field of Classification Search
None
See application file for complete search history.

(56) References Cited

U.S. PATENT DOCUMENTS

2010/0086550 A1  4/2010  Kang et al.

FOREIGN PATENT DOCUMENTS

| JP | 2010-83863 A | 4/2010 |
|---|---|---|
| JP | 2014-65748 A | 4/2014 |
| JP | 2014-65748 A5 | 9/2014 |
| JP | 2014-65748 A5 | 3/2015 |
| WO | 2013/173223 A1 | 11/2013 |
| WO | WO-2013173223 A1 * | 11/2013 ......... C07K 16/2827 |

OTHER PUBLICATIONS

Yokoyama, I., The Development of Antibody Formulations, etc. Related to PD-1 have been Intensified [TAT2013], Cancer Experts News, Nikkei Medical, Mar. 6, 2013, Retrieved Jun. 23, 2014 from http://medical.nikkeibp.co.jp/leaf/all/search/cancer/news/201303/529345.html.

Nonaka, N., Combination Use of Ipilimumab and Anti-PD-1 Antibody Drug, Nivolumab Shows a Noticeable and Continuous Tumor-Shrinking Effect on Half of Progressive Malignant Melanoma, Cancer Experts News, Nikkei Medical, May 17, 2013, Retrieved Jun. 23, 2014 from http://medical.nikkeibp.co.jp/leaf/all/search/cancer/news/201305/530569.html.

Topalian, S. et al., Safety, Activity, and Immune Correlates of Anti-PD-1 Antibody in Cancer, The New England Journal of Medicine, 2012, vol. 366, No. 26, pp. 2443-2454.

Maekawa, N. et al., Expression of PD-L1 on Canine Tumor Cells and Enhancement of IFN-γ Production from Tumor-Infiltrating Cells by PD-L1 Blockade, PLOS ONE, 2014, vol. 9, Issue 6, e98415.

English Translation of International Preliminary Report on Patentability and Written Opinion, dated Jan. 19, 2017, for PCT/JP2015/003444.

* cited by examiner

*Primary Examiner* — Sharon X Wen
(74) *Attorney, Agent, or Firm* — FisherBroyles, LLP; Robert Kinberg

(57) ABSTRACT

The object of the present invention is to provide an anti-canine PD-1 antibody or an anti-canine PD-L1 antibody, an agent for inhibiting binding between a canine PD-1 and a canine PD-L1 containing such an antibody, a method for inhibiting binding between a canine PD-1 and a canine PD-L1 comprising using such an antibody, and a gene encoding such an antibody. An anti-canine PD-1 antibody that specifically binds to a canine PD-1 consisting of the amino acid sequence set forth in SEQ ID NO: 1 and an anti-canine PD-L1 antibody that specifically binds to a canine PD-L1 consisting of the amino acid sequence set forth in SEQ ID NO: 6 are produced. An agent for inhibiting binding between a canine PD-1 and a canine PD-L1 containing such an antibody is also produced.

12 Claims, 7 Drawing Sheets
Specification includes a Sequence Listing.

[Figure 1]

```
                                                                    cctttt
            ccgctcacacctgtGCGGGAGCCGCCGGGGGAGGCGAGCAGGCGGGCTGGCGCTCCGGGC 66 ATGGGGAGCCGGCGGGGGCCCTGGCCGCTCGTCTGGGCCGTGCTGCAGCTGGGCTGGTGG
    1  M  G  S  R  R  G  P  W  P  L  V  W  A  V  L  Q  L  G  W  W 126 CCAGGATGGCTCCTAGACTCCCCTGACAGGCCCTGGAGCCCGCTCACCTTCTCCCCGGCG
   21  P  G  W  L  L  D  S  P  D  R  P  W  S  P  L  T  F  S  P  A 186 CAGCTCACGGTGCAGGAGGGAGAGAACGCCACGTTCACCTGCAGCCTGGCCGACATCCCC
   41  Q  L  T  V  Q  E  G  E  N  A  T  F  T  C  S  L  A  D  I  P 246 GACAGCTTCGTGCTCAACTGGTACCGCCTGAGCCCCCGCAACCAGACGGACAAGCTGGCC
   61  D  S  F  V  L  N  W  Y  R  L  S  P  R  N  Q  T  D  K  L  A 306 GCCTTCCAGGAGGACCGCATCGAGCCGGGCCGGGACAGGCGCTTCCGCGTCACGCGGCTG
   81  A  F  Q  E  D  R  I  E  P  G  R  D  R  R  F  R  V  T  R  L 366 CCCAACGGGCGGGACTTCCACATGAGCATCGTCGCTGCGCGCCTCAACGACAGCGGCATC
  101  P  N  G  R  D  F  H  M  S  I  V  A  A  R  L  N  D  S  G  I 426 TACCTGTGCGGGGCCATCTACCTGCCCCCCAACACACAGATCAACGAGAGTCCCCGCGCA
  121  Y  L  C  G  A  I  Y  L  P  P  N  T  Q  I  N  E  S  P  R  A 486 GAGCTCTCCGTGACGGAGAGAACCCTGGAGCCCCCCACACAGAGCCCCAGCCCCCCACCC
  141  E  L  S  V  T  E  R  T  L  E  P  P  T  Q  S  P  S  P  P  P 546 AGACTCAGCGGCCAGTTGCAGGGGCTGGTCATCGGCGTCACGAGCGTGCTGGTGGGTGTC
  161  R  L  S  G  Q  L  Q  G  L  V  I  G  V  T  S  V  L  V  G  V 606 CTGCTACTGCTGCTGCTGACCTGGGTCCTGGCCGCTGTCTTCCCCAGGGCCACCCGAGGT
  181  L  L  L  L  L  L  T  W  V  L  A  A  V  F  P  R  A  T  R  G 666 GCCTGTGTGTGCGGGAGCGAGGACGAGCCTCTGAAGGAGGGCCCCGATGCAGCGCCCGTC
  201  A  C  V  C  G  S  E  D  E  P  L  K  E  G  P  D  A  A  P  V 726 TTCACCCTGGACTACGGGGAGCTGGACTTCCAGTGGCGAGAGAAGACGCCGGAGCCCCCG
  221  F  T  L  D  Y  G  E  L  D  F  Q  W  R  E  K  T  P  E  P  P 786 GCGCCCTGTGCCCCGGAGCAGACCGAGTATGCCACCATCGTCTTCCCGGGCAGGCCGGCG
  241  A  P  C  A  P  E  Q  T  E  Y  A  T  I  V  F  P  G  R  P  A 846 TCCCCGGGCCGCAGGGCCTCGGCCAGCAGCCTGCAGGGAGCCCAGCCTCCGAGCCCCGAG
  261  S  P  G  R  R  A  S  A  S  S  L  Q  G  A  Q  P  P  S  P  E 906 GACGGACCCGGCCTGTGGCCCCCCTGACCGGCCGCCTCCGCTGGCCCATGTCCTGCAGAC
  281  D  G  P  G  L  W  P  P  *

TGTCCACCAGGAGCC
```

[Figure 2]

```
                                                CGGTGGTCACTTCAGAACG
 20 ATGAGAATGTTTAGTGTCTTTACATTCATGGCCTACTGCCATTTGCTAAAAGCATTTACG
  1  M  R  M  F  S  V  F  T  F  M  A  Y  C  H  L  L  K  A  F  T

80 ATCACAGTTTCTAAGGACCTGTATGTGGTAGAGTATGGTGGCAATGTGACAATGGAATGC
 21  I  T  V  S  K  D  L  Y  V  V  E  Y  G  G  N  V  T  M  E  C

140 AAATTCCCGGTGGAAAAACAGTTAAACTTGTTTGCACTAATCGTCTACTGGGAAATGGAG
 41  K  F  P  V  E  K  Q  L  N  L  F  A  L  I  V  Y  W  E  M  E

200 GATAAAAAAATTATACAATTTGTGAATGGAAAGGAAGACCTGAAAGTTCAGCACAGCAGC
 61  D  K  K  I  I  Q  F  V  N  G  K  E  D  L  K  V  Q  H  S  S

260 TACAGCCAGAGGGCTCAGCTATTGAAGGACCAGCTCTTCTTGGGGAAGGCTGCGCTTCAG
 81  Y  S  Q  R  A  Q  L  L  K  D  Q  L  F  L  G  K  A  A  L  Q

320 ATCACAGATGTGAGATTGCAGGATGCAGGGGTTTACTGCTGCTTGATCGGCTATGGCGGT
101  I  T  D  V  R  L  Q  D  A  G  V  Y  C  C  L  I  G  Y  G  G

380 GCTGACTACAAGCGGATTACTTTGAAAGTTCATGCCCCGTACCGCAACATCAGCCAAAGA
121  A  D  Y  K  R  I  T  L  K  V  H  A  P  Y  R  N  I  S  Q  R

440 ATTTCTGTGGATCCTGTCACCTCTGAACATGAACTAATGTGTCAGGCTGAGGGTTACCCT
141  I  S  V  D  P  V  T  S  E  H  E  L  M  C  Q  A  E  G  Y  P

500 GAGGCTGAAGTCATCTGGACAAGCAGTGACCACCGAGTCCTGAGTGGCAAAACCACCATC
161  E  A  E  V  I  W  T  S  S  D  H  R  V  L  S  G  K  T  T  I

560 ACTAATTCCAATAGGGAAGAGAAGCTTTTCAATGTGACCAGCACGCTGAACATCAATGCA
181  T  N  S  N  R  E  E  K  L  F  N  V  T  S  T  L  N  I  N  A

620 ACAGCTAATGAGATTTTCTACTGCACTTTTCAAAGATCAGGTCCTGAGGAAAACAATACT
201  T  A  N  E  I  F  Y  C  T  F  Q  R  S  G  P  E  E  N  N  T

680 GCCGAGTTGGTCATCCCAGAACGACTGCCCGTTCCAGCAAGTGAGAGGACTCATTTCATG
221  A  E  L  V  I  P  E  R  L  P  V  P  A  S  E  R  T  H  F  M

740 ATTCTGGGACCTTTCCTGTTGCTTCTTGGTGTAGTCCTGGCAGTCACTTTCTGTCTAAAA
241  I  L  G  P  F  L  L  L  L  G  V  V  L  A  V  T  F  C  L  K

800 AAACATGGGAGAATGATGGATGTGGAAAAATGTTGCACCCGAGATAGGAACTCAAAGAAA
261  K  H  G  R  M  M  D  V  E  K  C  C  T  R  D  R  N  S  K  K

860 CGAAATGATATACAATTTGAAGAGACATAATCCAGCATGGAAACTCCTGATCTTAAAGCA
281  R  N  D  I  Q  F  E  E  T  *

GGGATTCTCGGCCTGTGGTTTGAGTTCAGCA
```

[Figure 3]
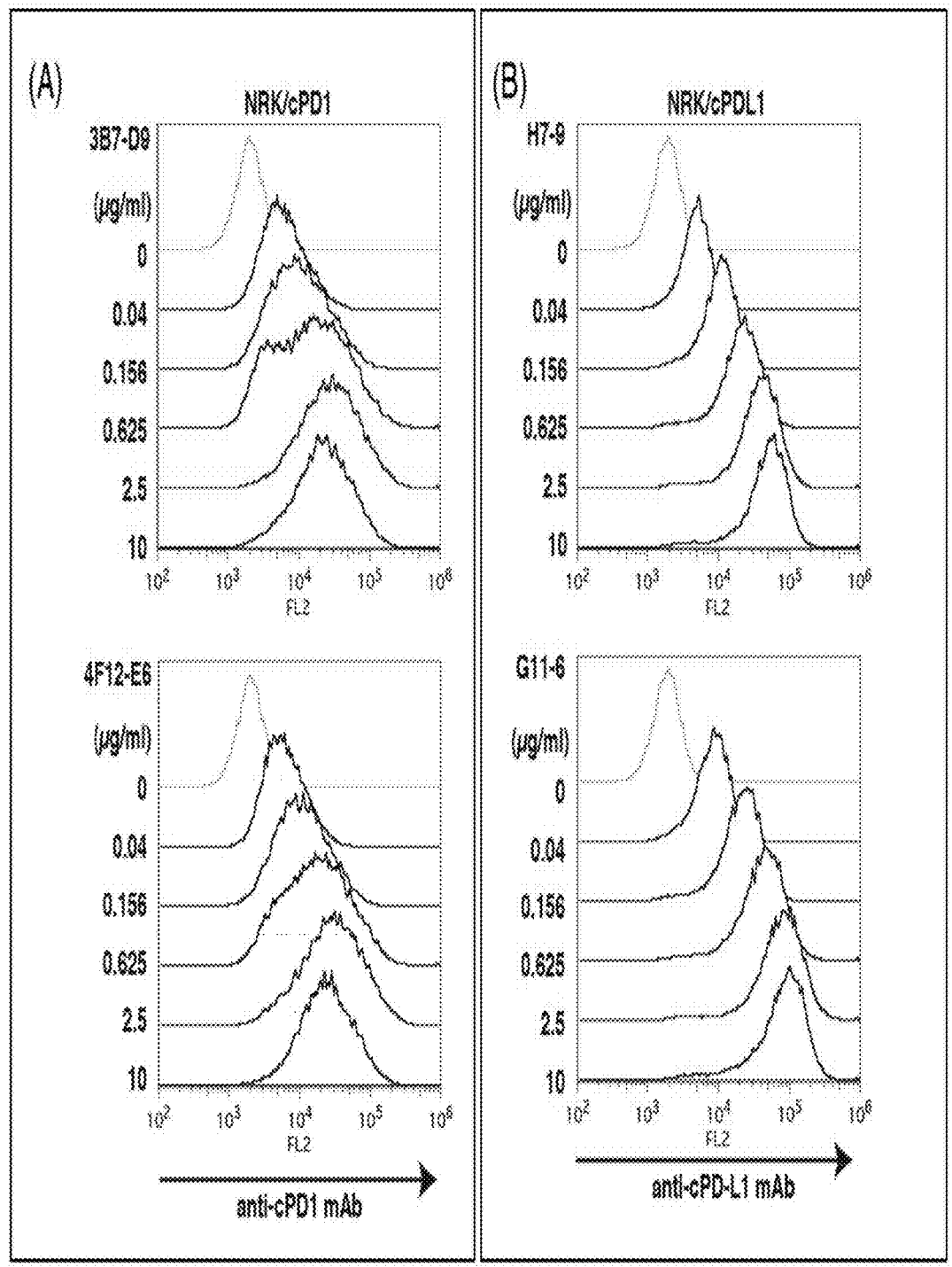

[Figure 4]
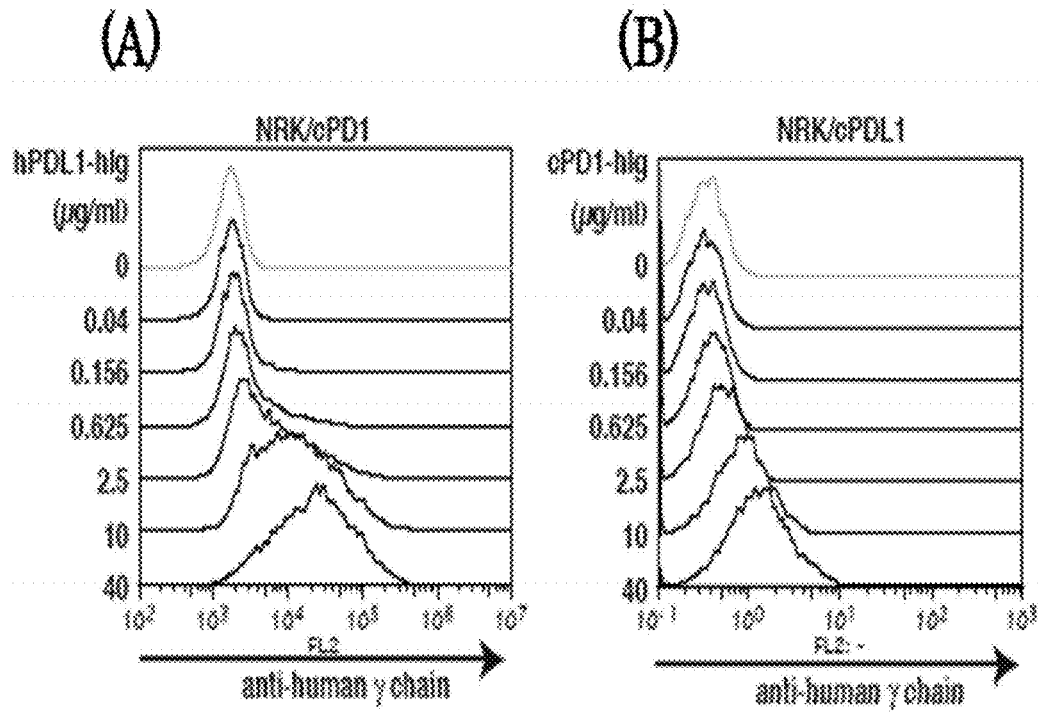
[Figure 5]
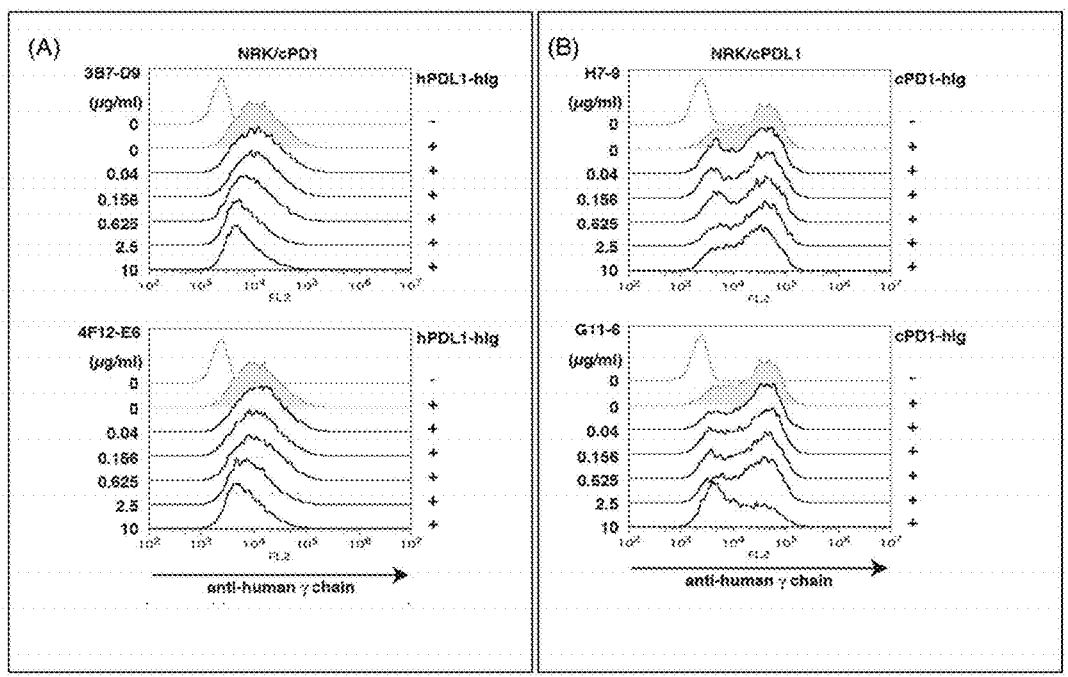

[Figure 6]
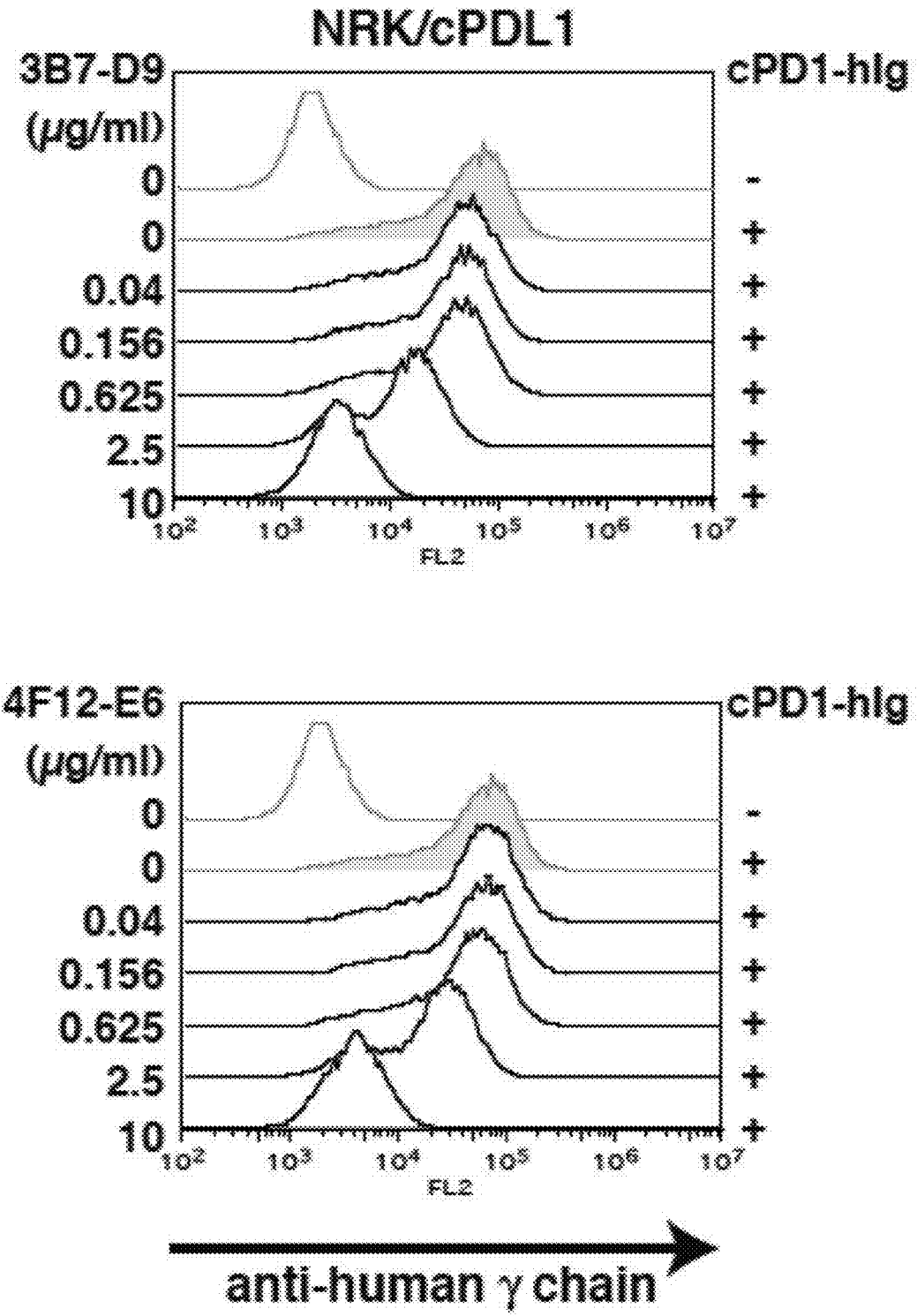

[Figure 7]
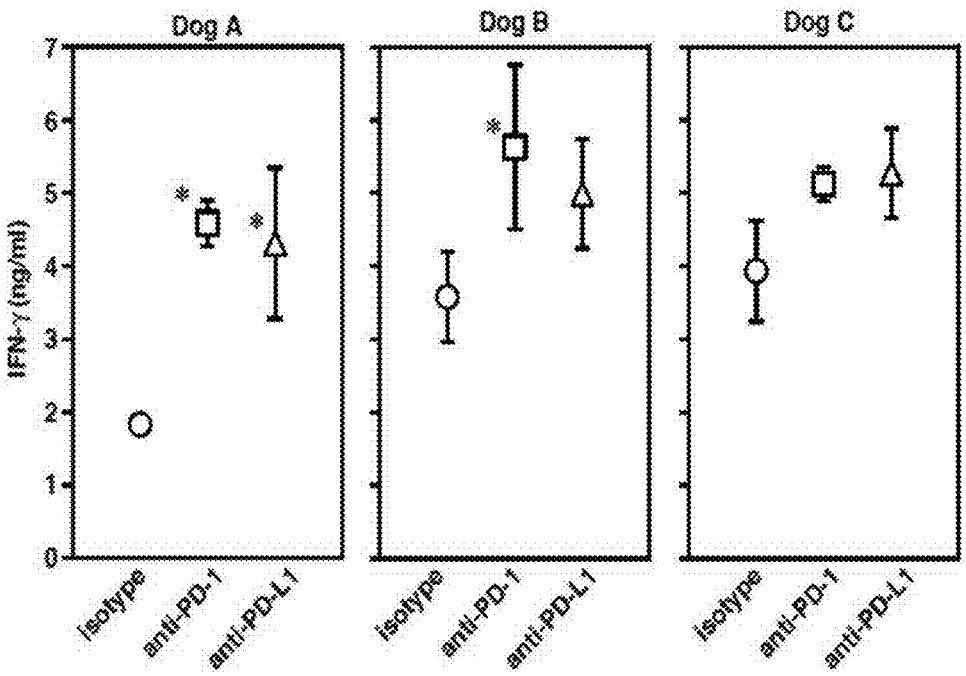
[Figure 8]
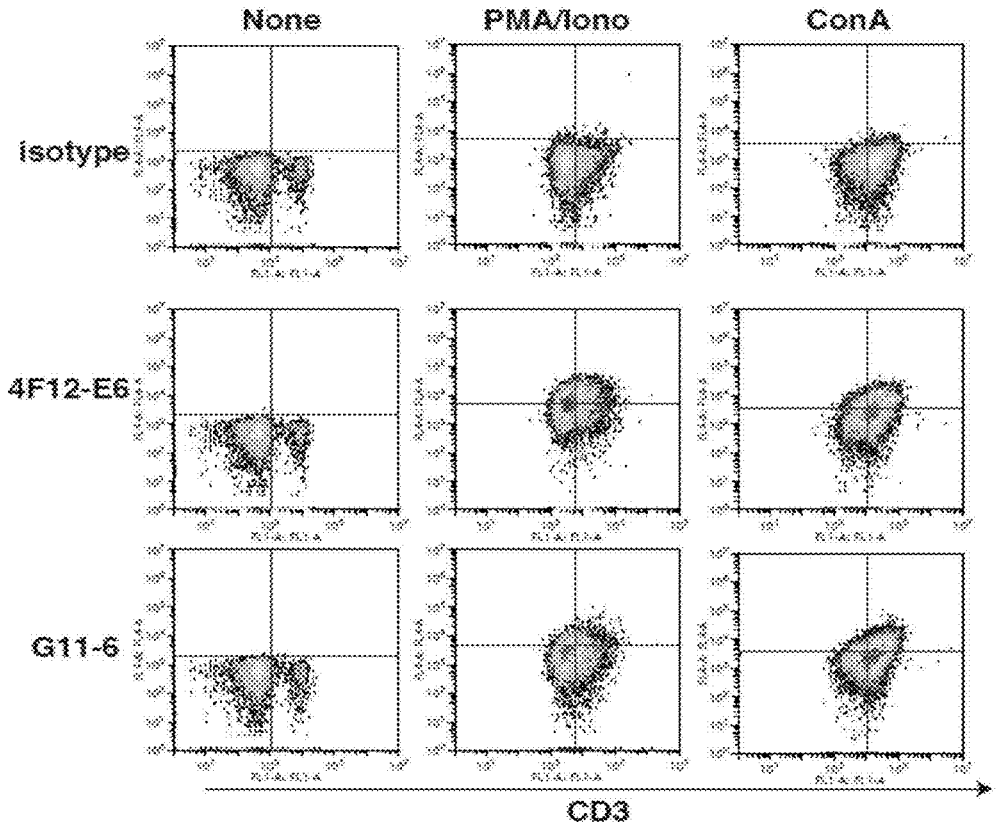

[Figure 9]
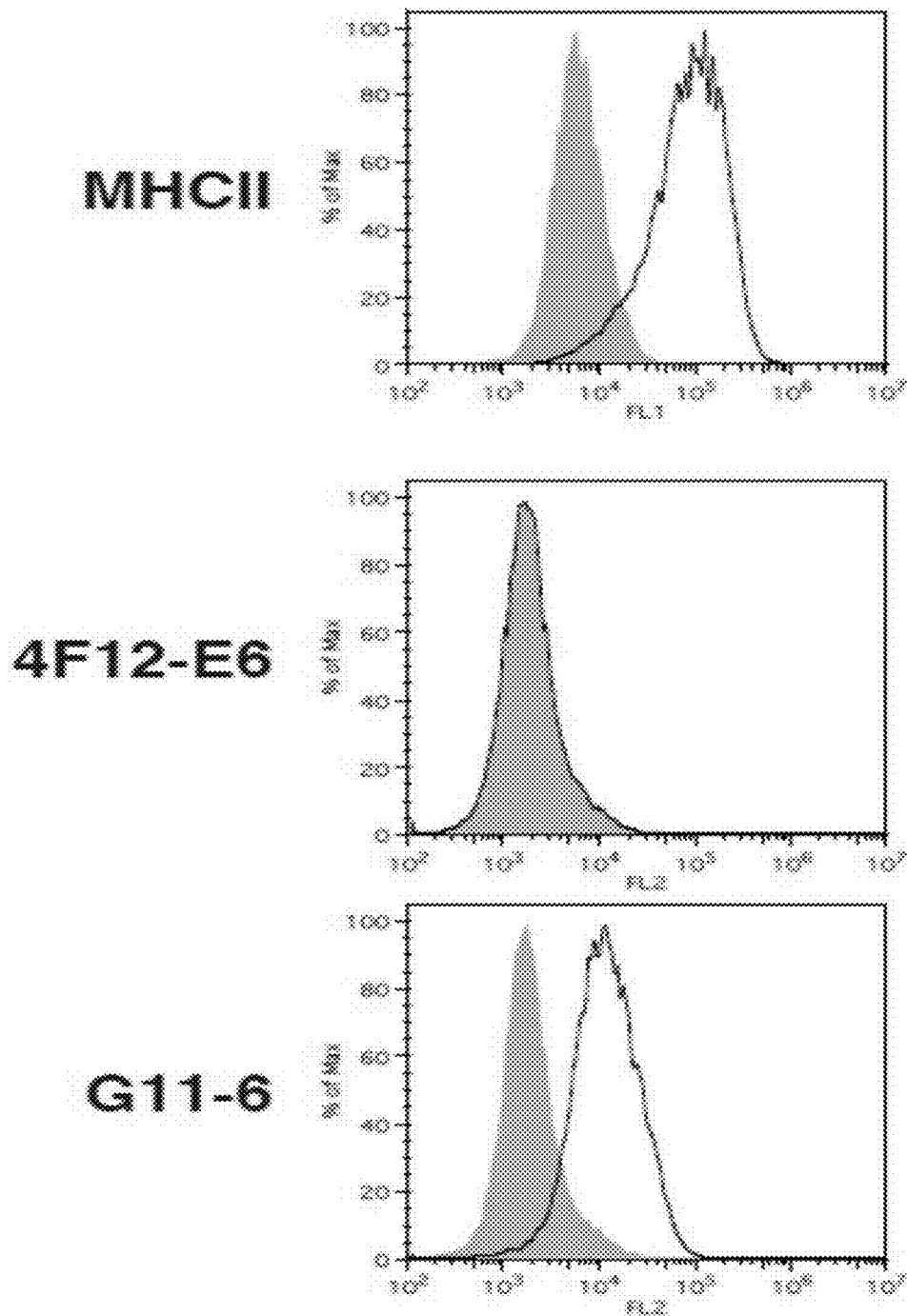

SEQUENCE LISTING

```
<160> NUMBER OF SEQ ID NOS: 66

<210> SEQ ID NO 1
<211> LENGTH: 288
<212> TYPE: PRT
<213> ORGANISM: artificial
<220> FEATURE:
<223> OTHER INFORMATION: cPD1 aa
<220> FEATURE:
<223> OTHER INFORMATION: Inventor: Mizuno, Takuya
      Inventor: Shosu, Kazuha

<400> SEQUENCE: 1

Met Gly Ser Arg Arg Gly Pro Trp Pro Leu Val Trp Ala Val Leu Gln
1               5                   10                  15

Leu Gly Trp Trp Pro Gly Trp Leu Leu Asp Ser Pro Asp Arg Pro Trp
            20                  25                  30
```

Ser Pro Leu Thr Phe Ser Pro Ala Gln Leu Thr Val Gln Glu Gly Glu
        35                  40                  45

Asn Ala Thr Phe Thr Cys Ser Leu Ala Asp Ile Pro Asp Ser Phe Val
 50                  55                  60

Leu Asn Trp Tyr Arg Leu Ser Pro Arg Asn Gln Thr Asp Lys Leu Ala
 65                  70                  75                  80

Ala Phe Gln Glu Asp Arg Ile Glu Pro Gly Arg Asp Arg Arg Phe Arg
                 85                  90                  95

Val Thr Arg Leu Pro Asn Gly Arg Asp Phe His Met Ser Ile Val Ala
                100                 105                 110

Ala Arg Leu Asn Asp Ser Gly Ile Tyr Leu Cys Gly Ala Ile Tyr Leu
            115                 120                 125

Pro Pro Asn Thr Gln Ile Asn Glu Ser Pro Arg Ala Glu Leu Ser Val
        130                 135                 140

Thr Glu Arg Thr Leu Glu Pro Pro Thr Gln Ser Pro Ser Pro Pro Pro
145                 150                 155                 160

Arg Leu Ser Gly Gln Leu Gln Gly Leu Val Ile Gly Val Thr Ser Val
                165                 170                 175

Leu Val Gly Val Leu Leu Leu Leu Leu Thr Trp Val Leu Ala Ala
                180                 185                 190

Val Phe Pro Arg Ala Thr Arg Gly Ala Cys Val Cys Gly Ser Glu Asp
            195                 200                 205

Glu Pro Leu Lys Glu Gly Pro Asp Ala Ala Pro Val Phe Thr Leu Asp
        210                 215                 220

Tyr Gly Glu Leu Asp Phe Gln Trp Arg Glu Lys Thr Pro Glu Pro Pro
225                 230                 235                 240

Ala Pro Cys Ala Pro Glu Gln Thr Glu Tyr Ala Thr Ile Val Phe Pro
                245                 250                 255

Gly Arg Pro Ala Ser Pro Gly Arg Arg Ala Ser Ala Ser Ser Leu Gln
                260                 265                 270

Gly Ala Gln Pro Pro Ser Pro Glu Asp Gly Pro Gly Leu Trp Pro Pro
            275                 280                 285

<210> SEQ ID NO 2
<211> LENGTH: 139
<212> TYPE: PRT
<213> ORGANISM: artificial
<220> FEATURE:
<223> OTHER INFORMATION: 3B7-D9 IgH V region aa

<400> SEQUENCE: 2

Met Ala Ile Arg Leu Ser Leu Val Phe Leu Val Leu Phe Ile Lys Gly
 1               5                  10                  15

Val Gln Cys Glu Val Gln Leu Val Glu Thr Gly Gly Gly Leu Val Gln
                20                  25                  30

Pro Gly Arg Ser Leu Lys Leu Ser Cys Val Ala Ser Gly Phe Thr Phe
            35                  40                  45

Asn Asn Tyr Trp Met Ser Trp Thr Arg Gln Ala Pro Gly Lys Gly Leu
 50                  55                  60

Glu Trp Val Ala Ser Ile Thr Asn Ser Gly Val Ser Thr Tyr Tyr Pro
 65                  70                  75                  80

Asp Ser Val Lys Gly Arg Phe Thr Ile Ser Arg Asp Asn Ala Gln Asn
                 85                  90                  95

Thr Leu Tyr Leu Gln Met Asn Ser Leu Arg Ser Glu Asp Thr Ala Thr
                100                 105                 110

```
Tyr Phe Cys Thr Ser Ala Leu Asn Trp Gly Tyr Trp Tyr Phe Asp Phe
            115                 120                 125

Trp Gly Pro Gly Thr Met Val Thr Val Ser Ser
            130                 135

<210> SEQ ID NO 3
<211> LENGTH: 133
<212> TYPE: PRT
<213> ORGANISM: artificial
<220> FEATURE:
<223> OTHER INFORMATION: 3B7-D9 Igkappa V region aa

<400> SEQUENCE: 3

Met Glu Ser Gln Thr Gln Val Leu Met Ser Leu Leu Leu Trp Val Ser
 1               5                  10                  15

Gly Thr Cys Gly Asp Ile Val Met Thr Gln Thr Pro Ser Ser Gln Ala
                20                  25                  30

Val Ser Ala Gly Glu Lys Val Thr Met Ser Cys Lys Ser Ser Gln Ser
            35                  40                  45

Leu Leu Tyr Ser Glu Asn Lys Lys Asn Tyr Leu Ala Trp Tyr Gln Arg
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Tyr Tyr Asn Phe Pro Leu Thr Phe Gly Ser Gly Thr
        115                 120                 125

Lys Leu Glu Ile Lys
    130

<210> SEQ ID NO 4
<211> LENGTH: 139
<212> TYPE: PRT
<213> ORGANISM: artificial
<220> FEATURE:
<223> OTHER INFORMATION: 4F12-E6 IgH V region aa

<400> SEQUENCE: 4

Met Ala Ile Arg Leu Ser Leu Val Phe Leu Val Leu Phe Ile Lys Gly
 1               5                  10                  15

Val Gln Cys Glu Val Gln Leu Val Glu Thr Gly Gly Gly Leu Val Gln
                20                  25                  30

Pro Gly Arg Ser Leu Lys Leu Ser Cys Val Ala Ser Gly Phe Thr Phe
            35                  40                  45

Asn Asn Tyr Trp Met Thr Trp Arg Gln Ala Pro Gly Lys Gly Leu
    50                  55                  60

Glu Trp Val Ala Ser Ile Thr Asn Ser Gly Val Ser Thr Tyr Tyr Pro
65                  70                  75                  80

Asp Ser Val Lys Gly Arg Phe Thr Ile Ser Arg Asp Asn Ala Gln Asn
                85                  90                  95

Thr Leu Tyr Leu Gln Met Asn Ser Leu Arg Ser Glu Thr Ala Thr
            100                 105                 110

Tyr Tyr Cys Thr Ser Ala Leu Asn Trp Gly Tyr Trp Tyr Phe Asp Phe
        115                 120                 125

Trp Gly Pro Gly Thr Met Val Thr Val Ser Ser
    130                 135
```

<210> SEQ ID NO 5
<211> LENGTH: 133
<212> TYPE: PRT
<213> ORGANISM: artificial
<220> FEATURE:
<223> OTHER INFORMATION: 4F12-E6 Igkappa V region aa

<400> SEQUENCE: 5

Met Glu Ser Gln Thr Gln Val Leu Met Ser Leu Leu Trp Val Ser
1               5                   10                  15

Gly Thr Cys Gly Asp Ile Val Met Thr Gln Thr Pro Ser Ser Gln Ala
            20                  25                  30

Val Ser Ala Gly Glu Lys Val Thr Met Ser Cys Lys Ser Ser Gln Ser
        35                  40                  45

Leu Leu Tyr Ser Glu Asn Lys Lys Asn Tyr Leu Ala Trp Tyr Gln Gln
    50                  55                  60

Lys Pro Gly Gln Ser Pro Lys Leu Leu Ile Tyr Trp Ala Ser Thr Arg
65                  70                  75                  80

Glu Ser Gly Val Pro Asp Arg Phe Ile Gly Ser Gly Ser Gly Thr Asp
                85                  90                  95

Phe Thr Leu Thr Ile Ser Ser Val Gln Ala Glu Asp Leu Ala Val Tyr
            100                 105                 110

Tyr Cys Gln Gln Tyr Tyr Asn Phe Pro Leu Thr Phe Gly Ser Gly Thr
        115                 120                 125

Lys Leu Glu Ile Lys
    130

<210> SEQ ID NO 6
<211> LENGTH: 289
<212> TYPE: PRT
<213> ORGANISM: artificial
<220> FEATURE:
<223> OTHER INFORMATION: cPDL1 aa

<400> SEQUENCE: 6

Met Arg Met Phe Ser Val Phe Thr Phe Met Ala Tyr Cys His Leu Leu
1               5                   10                  15

Lys Ala Phe Thr Ile Thr Val Ser Lys Asp Leu Tyr Val Val Glu Tyr
            20                  25                  30

Gly Gly Asn Val Thr Met Glu Cys Lys Phe Pro Val Glu Lys Gln Leu
        35                  40                  45

Asn Leu Phe Ala Leu Ile Val Tyr Trp Glu Met Glu Asp Lys Lys Ile
    50                  55                  60

Ile Gln Phe Val Asn Gly Lys Glu Asp Leu Lys Val Gln His Ser Ser
65                  70                  75                  80

Tyr Ser Gln Arg Ala Gln Leu Leu Lys Asp Gln Leu Phe Leu Gly Lys
                85                  90                  95

Ala Ala Leu Gln Ile Thr Asp Val Arg Leu Gln Asp Ala Gly Val Tyr
            100                 105                 110

Cys Cys Leu Ile Gly Tyr Gly Gly Ala Asp Tyr Lys Arg Ile Thr Leu
        115                 120                 125

Lys Val His Ala Pro Tyr Arg Asn Ile Ser Gln Arg Ile Ser Val Asp
    130                 135                 140

Pro Val Thr Ser Glu His Glu Leu Met Cys Gln Ala Glu Gly Tyr Pro
145                 150                 155                 160

Glu Ala Glu Val Ile Trp Thr Ser Ser Asp His Arg Val Leu Ser Gly

```
                      165                 170                 175
Lys Thr Thr Ile Thr Asn Ser Asn Arg Glu Glu Lys Leu Phe Asn Val
                  180                 185                 190

Thr Ser Thr Leu Asn Ile Asn Ala Thr Ala Asn Glu Ile Phe Tyr Cys
              195                 200                 205

Thr Phe Gln Arg Ser Gly Pro Glu Glu Asn Asn Thr Ala Glu Leu Val
          210                 215                 220

Ile Pro Glu Arg Leu Pro Val Pro Ala Ser Glu Arg Thr His Phe Met
225                 230                 235                 240

Ile Leu Gly Pro Phe Leu Leu Leu Gly Val Val Leu Ala Val Thr
                  245                 250                 255

Phe Cys Leu Lys Lys His Gly Arg Met Met Asp Val Glu Lys Cys Cys
                  260                 265                 270

Thr Arg Asp Arg Asn Ser Lys Lys Arg Asn Asp Ile Gln Phe Glu Glu
              275                 280                 285

Thr
```

<210> SEQ ID NO 7
<211> LENGTH: 137
<212> TYPE: PRT
<213> ORGANISM: artificial
<220> FEATURE:
<223> OTHER INFORMATION: H7-9 IgH V region aa

<400> SEQUENCE: 7

```
Met Ala Val Leu Val Leu Leu Cys Leu Val Thr Phe Pro Ser Cys
1               5                   10                  15

Val Leu Ser Gln Val Gln Leu Lys Glu Ser Gly Pro Gly Leu Val Gln
                20                  25                  30

Pro Ser Gln Thr Leu Ser Leu Thr Cys Thr Val Ser Gly Phe Ser Leu
            35                  40                  45

Thr Ser Tyr Thr Val Ser Trp Val Arg Gln Pro Pro Gly Lys Gly Leu
        50                  55                  60

Glu Trp Ile Ala Ala Ile Ser Ser Gly Gly Asn Thr Tyr Ser Asn Ser
65                  70                  75                  80

Ala Leu Lys Ser Arg Leu Ser Ile Ser Arg Asp Thr Ser Lys Ser Gln
                85                  90                  95

Phe Phe Leu Lys Met Asn Ser Leu Gln Thr Glu Asp Thr Ala Met Tyr
            100                 105                 110

Phe Cys Ala Arg Glu Gly Tyr Tyr Gly Tyr Asn Phe Asp Tyr Trp Gly
        115                 120                 125

Gln Gly Val Met Val Thr Val Ser Ser
    130                 135
```

<210> SEQ ID NO 8
<211> LENGTH: 127
<212> TYPE: PRT
<213> ORGANISM: artificial
<220> FEATURE:
<223> OTHER INFORMATION: H7-9 Igkappa V region aa

<400> SEQUENCE: 8

```
Met Glu Ser His Thr Arg Val Phe Ile Phe Leu Leu Leu Trp Leu Ser
1               5                   10                  15

Gly Ala Asp Gly Asp Ile Val Met Thr Gln Ser Pro Thr Ser Met Ser
                20                  25                  30

Ile Ser Val Gly Asp Arg Val Thr Met Asn Cys Lys Ala Ser Gln Asn
```

```
                    35                  40                  45

Val Gly Ser Asn Val Asp Trp Tyr Gln Gln Lys Thr Gly Gln Ser Pro
        50                  55                  60

Lys Leu Leu Ile Tyr Lys Ala Ser Asn Arg Tyr Thr Gly Val Pro Asp
 65                  70                  75                  80

Arg Phe Thr Gly Ser Gly Ser Gly Thr Asp Phe Thr Phe Thr Ile Ser
                85                  90                  95

Asn Met Gln Ala Glu Asp Leu Ala Val Tyr Tyr Cys Met Gln Ser Asn
            100                 105                 110

Ser Tyr Pro Leu Thr Phe Gly Ser Gly Thr Lys Leu Glu Ile Lys
        115                 120                 125

<210> SEQ ID NO 9
<211> LENGTH: 139
<212> TYPE: PRT
<213> ORGANISM: artificial
<220> FEATURE:
<223> OTHER INFORMATION: G11-6 IgH V region aa

<400> SEQUENCE: 9

Met Asp Thr Arg Leu Ser Leu Val Phe Leu Val Leu Phe Ile Lys Gly
 1               5                  10                  15

Val Gln Cys Glu Val Gln Leu Val Glu Ser Gly Gly Gly Leu Val Gln
            20                  25                  30

Pro Gly Arg Ser Leu Lys Leu Ser Cys Ala Ala Ser Gly Phe Thr Phe
        35                  40                  45

Ser Asp Tyr Tyr Met Ala Trp Val Arg Gln Ala Pro Lys Lys Gly Leu
    50                  55                  60

Glu Trp Val Ala Ser Ile Ser Tyr Glu Asp Ser Ser Thr Tyr Tyr Gly
 65                  70                  75                  80

Asp Ser Val Lys Gly Arg Phe Thr Ile Ser Arg Asp Asn Ala Lys Ser
                85                  90                  95

Thr Leu Tyr Leu Gln Met Asn Ser Leu Arg Ser Glu Asp Thr Ala Thr
            100                 105                 110

Tyr Tyr Cys Ala Arg Ser Ala Trp Asn Tyr Pro Tyr Trp Phe Ala Tyr
        115                 120                 125

Trp Gly Gln Gly Thr Leu Val Thr Val Ser Ser
    130                 135

<210> SEQ ID NO 10
<211> LENGTH: 127
<212> TYPE: PRT
<213> ORGANISM: artificial
<220> FEATURE:
<223> OTHER INFORMATION: G11-6 Igkappa V region aa

<400> SEQUENCE: 10

Met Glu Ser Tyr Thr Arg Val Phe Ile Phe Leu Leu Leu Trp Leu Ser
 1               5                  10                  15

Gly Ala Asp Gly Asn Thr Val Met Thr Gln Ser Pro Thr Ser Met Phe
            20                  25                  30

Ile Ser Val Gly Asp Arg Val Thr Val Asn Cys Lys Ala Ser Gln Asn
        35                  40                  45

Val Gly Thr Asn Val Asp Trp Tyr Gln Gln Lys Thr Gly Gln Ser Pro
    50                  55                  60

Lys Leu Leu Ile Tyr Gly Ala Ser Asn Arg Tyr Thr Gly Val Pro Asp
 65                  70                  75                  80
```

```
            Arg Phe Thr Gly Ser Gly Ser Gly Thr Asp Phe Thr Leu Thr Ile Ser
                         85                  90                  95

Asn Met Gln Ala Glu Asp Leu Ala Val Tyr Tyr Cys Leu Gln Tyr Asn
                        100                 105                 110

Tyr Asn Pro Trp Thr Phe Gly Gly Thr Lys Leu Glu Leu Lys
                    115                 120                 125

<210> SEQ ID NO 11
<211> LENGTH: 8
<212> TYPE: PRT
<213> ORGANISM: artificial
<220> FEATURE:
<223> OTHER INFORMATION: 3B7-D9 IgH V region CDR1 aa

<400> SEQUENCE: 11

Gly Phe Thr Phe Asn Asn Tyr Trp
1               5

<210> SEQ ID NO 12
<211> LENGTH: 8
<212> TYPE: PRT
<213> ORGANISM: artificial
<220> FEATURE:
<223> OTHER INFORMATION: 3B7-D9 IgH V region CDR2 aa

<400> SEQUENCE: 12

Ile Thr Asn Ser Gly Val Ser Thr
1               5

<210> SEQ ID NO 13
<211> LENGTH: 13
<212> TYPE: PRT
<213> ORGANISM: artificial
<220> FEATURE:
<223> OTHER INFORMATION: 3B7-D9 IgH V region CDR3 aa

<400> SEQUENCE: 13

Thr Ser Ala Leu Asn Trp Gly Tyr Trp Tyr Phe Asp Phe
1               5                   10

<210> SEQ ID NO 14
<211> LENGTH: 12
<212> TYPE: PRT
<213> ORGANISM: artificial
<220> FEATURE:
<223> OTHER INFORMATION: 3B7-D9 Igkappa V region CDR1 aa

<400> SEQUENCE: 14

Leu Leu Tyr Ser Glu Asn Lys Lys Asn Tyr Leu Ala
1               5                   10

<210> SEQ ID NO 15
<211> LENGTH: 3
<212> TYPE: PRT
<213> ORGANISM: artificial
<220> FEATURE:
<223> OTHER INFORMATION: 3B7-D9 Igkappa V region CDR2 aa

<400> SEQUENCE: 15

Trp Ala Ser
1

<210> SEQ ID NO 16
<211> LENGTH: 6
<212> TYPE: PRT
<213> ORGANISM: artificial
```

```
<220> FEATURE:
<223> OTHER INFORMATION: 3B7-D9 Igkappa V region CDR3 aa

<400> SEQUENCE: 16

Tyr Tyr Asn Phe Pro Leu
1               5

<210> SEQ ID NO 17
<211> LENGTH: 8
<212> TYPE: PRT
<213> ORGANISM: artificial
<220> FEATURE:
<223> OTHER INFORMATION: 4F12-E6 IgH V region CDR1 aa

<400> SEQUENCE: 17

Gly Phe Thr Phe Asn Asn Tyr Trp
1               5

<210> SEQ ID NO 18
<211> LENGTH: 8
<212> TYPE: PRT
<213> ORGANISM: artificial
<220> FEATURE:
<223> OTHER INFORMATION: 4F12-E6 IgH V region CDR2 aa

<400> SEQUENCE: 18

Ile Thr Asn Ser Gly Val Ser Thr
1               5

<210> SEQ ID NO 19
<211> LENGTH: 13
<212> TYPE: PRT
<213> ORGANISM: artificial
<220> FEATURE:
<223> OTHER INFORMATION: 4F12-E6 IgH V region CDR3 aa

<400> SEQUENCE: 19

Thr Ser Ala Leu Asn Trp Gly Tyr Trp Tyr Phe Asp Phe
1               5                   10

<210> SEQ ID NO 20
<211> LENGTH: 10
<212> TYPE: PRT
<213> ORGANISM: artificial
<220> FEATURE:
<223> OTHER INFORMATION: 4F12-E6 Igkappa V region CDR1 aa

<400> SEQUENCE: 20

Leu Leu Tyr Ser Glu Asn Lys Lys Asn Tyr
1               5                   10

<210> SEQ ID NO 21
<211> LENGTH: 3
<212> TYPE: PRT
<213> ORGANISM: artificial
<220> FEATURE:
<223> OTHER INFORMATION: 4F12-E6 Igkappa V region CDR2 aa

<400> SEQUENCE: 21

Trp Ala Ser
1

<210> SEQ ID NO 22
<211> LENGTH: 6
<212> TYPE: PRT
<213> ORGANISM: artificial
<220> FEATURE:
```

<223> OTHER INFORMATION: 4F12-E6 Igkappa V region CDR3 aa

<400> SEQUENCE: 22

Tyr Tyr Asn Phe Pro Leu
1               5

<210> SEQ ID NO 23
<211> LENGTH: 8
<212> TYPE: PRT
<213> ORGANISM: artificial
<220> FEATURE:
<223> OTHER INFORMATION: H7-9 IgH V region CDR1 aa

<400> SEQUENCE: 23

Gly Phe Ser Leu Thr Ser Tyr Thr
1               5

<210> SEQ ID NO 24
<211> LENGTH: 7
<212> TYPE: PRT
<213> ORGANISM: artificial
<220> FEATURE:
<223> OTHER INFORMATION: H7-9 IgH V region CDR2 aa

<400> SEQUENCE: 24

Ile Ser Ser Gly Gly Asn Thr
1               5

<210> SEQ ID NO 25
<211> LENGTH: 12
<212> TYPE: PRT
<213> ORGANISM: artificial
<220> FEATURE:
<223> OTHER INFORMATION: H7-9 IgH V region CDR3 aa

<400> SEQUENCE: 25

Ala Arg Glu Gly Tyr Tyr Gly Tyr Asn Phe Asp Tyr
1               5                   10

<210> SEQ ID NO 26
<211> LENGTH: 6
<212> TYPE: PRT
<213> ORGANISM: artificial
<220> FEATURE:
<223> OTHER INFORMATION: H7-9 Igkappa V region CDR1 aa

<400> SEQUENCE: 26

Gln Asn Val Gly Ser Asn
1               5

<210> SEQ ID NO 27
<211> LENGTH: 3
<212> TYPE: PRT
<213> ORGANISM: artificial
<220> FEATURE:
<223> OTHER INFORMATION: H7-9 Igkappa V region CDR2 aa

<400> SEQUENCE: 27

Lys Ala Ser
1

<210> SEQ ID NO 28
<211> LENGTH: 6
<212> TYPE: PRT
<213> ORGANISM: artificial
<220> FEATURE:
<223> OTHER INFORMATION: H7-9 Igkappa V region CDR3 aa

```
<400> SEQUENCE: 28

Ser Asn Ser Tyr Pro Leu
1               5

<210> SEQ ID NO 29
<211> LENGTH: 8
<212> TYPE: PRT
<213> ORGANISM: artificial
<220> FEATURE:
<223> OTHER INFORMATION: G11-6 IgH V region CDR1 aa

<400> SEQUENCE: 29

Gly Phe Thr Phe Ser Asp Tyr Tyr
1               5

<210> SEQ ID NO 30
<211> LENGTH: 8
<212> TYPE: PRT
<213> ORGANISM: artificial
<220> FEATURE:
<223> OTHER INFORMATION: G11-6 IgH V region CDR2 aa

<400> SEQUENCE: 30

Ile Ser Tyr Glu Asp Ser Ser Thr
1               5

<210> SEQ ID NO 31
<211> LENGTH: 13
<212> TYPE: PRT
<213> ORGANISM: artificial
<220> FEATURE:
<223> OTHER INFORMATION: G11-6 IgH V region CDR3 aa

<400> SEQUENCE: 31

Ala Arg Ser Ala Trp Asn Tyr Pro Tyr Trp Phe Ala Tyr
1               5                   10

<210> SEQ ID NO 32
<211> LENGTH: 6
<212> TYPE: PRT
<213> ORGANISM: artificial
<220> FEATURE:
<223> OTHER INFORMATION: G11-6 Igkappa V region CDR1 aa

<400> SEQUENCE: 32

Gln Asn Val Gly Thr Asn
1               5

<210> SEQ ID NO 33
<211> LENGTH: 3
<212> TYPE: PRT
<213> ORGANISM: artificial
<220> FEATURE:
<223> OTHER INFORMATION: G11-6 Igkappa V region CDR2 aa

<400> SEQUENCE: 33

Gly Ala Ser
1

<210> SEQ ID NO 34
<211> LENGTH: 6
<212> TYPE: PRT
<213> ORGANISM: artificial
<220> FEATURE:
<223> OTHER INFORMATION: G11-6 Igkappa V region CDR3 aa
```

<400> SEQUENCE: 34

Tyr Asn Tyr Asn Pro Trp
1               5

<210> SEQ ID NO 35
<211> LENGTH: 417
<212> TYPE: DNA
<213> ORGANISM: artificial
<220> FEATURE:
<223> OTHER INFORMATION: 3B7-D9 IgH V region nt

<400> SEQUENCE: 35

```
atggccatca ggctcagctt ggttttcctt gtccttttca taaaaggtgt ccagtgtgaa    60
gtgcagctgg tggagactgg gggaggccta gtgcagcctg aaggtctct gaaactctcc   120
tgtgtagcct ctggattcac gttcaataac tactggatga gctggacccg ccaggctcca   180
gggaaggggc tggagtgggt tgcatccatt actaatagtg gtgttagcac ttactatcca   240
gactctgtga aggccgatt cactatttcc agagataatg cacaaaacac cctatacctg   300
caaatgaaca gtctgaggtc tgaggacacg gccacttatt tctgtacaag cgcacttaac   360
tggggctact ggtactttga cttctggggc caggaaccat ggtcaccgt gtcttca       417
```

<210> SEQ ID NO 36
<211> LENGTH: 399
<212> TYPE: DNA
<213> ORGANISM: artificial
<220> FEATURE:
<223> OTHER INFORMATION: 3B7-D9 Igkappa V region nt

<400> SEQUENCE: 36

```
atggaatcac agacccaggt cctcatgtcc ctgctgctct gggtatctgg tacctgtggg    60
gacattgtga tgacccagac tccatcctcc caggctgtgt cagcagggga aaggtcact   120
atgagctgca gtccagtca gagtctttta tacagtgaaa acaagaagaa ctacttggcc   180
tggtaccagc ggaaaccagg gcagtctcct aaactgctga tctactgggc atccactagg   240
gaatctgggg tccctgatcg cttcataggc agtggatctg gacagatttt cactctgacc   300
atcagcagtg tgcaggcaga agacctggct gtttattact gccagcagta ctataacttt   360
ccgctcacgt tcggttctgg gaccaagctg gagatcaaa                          399
```

<210> SEQ ID NO 37
<211> LENGTH: 417
<212> TYPE: DNA
<213> ORGANISM: artificial
<220> FEATURE:
<223> OTHER INFORMATION: 4F12-E6 IgH V region nt

<400> SEQUENCE: 37

```
atggccatca ggctcagctt ggttttcctt gtccttttca taaaaggtgt ccagtgtgaa    60
gtgcagctgg tggagactgg gggaggccta gtgcagcctg aaggtctct gaaactctcc   120
tgtgtagcct ctggattcac gttcaataac tactggatga cctggacccg ccaggctcca   180
gggaaggggc tggagtgggt tgcatccatt actaatagtg gtgttagcac ttactatcca   240
gactctgtga aggccgatt cactatctcc agagataatg cacaaaacac cctatacctg   300
caaatgaaca gtctgaggtc tgaggacacg gccacttatt actgtacaag cgcacttaac   360
tggggctact ggtactttga cttctggggc caggaaccat ggtcaccgt gtcctca       417
```

<210> SEQ ID NO 38

```
<211> LENGTH: 399
<212> TYPE: DNA
<213> ORGANISM: artificial
<220> FEATURE:
<223> OTHER INFORMATION: 4F12-E6 Igkappa V region nt

<400> SEQUENCE: 38
atggaatcac agacccaggt cctcatgtcc ctgctgctct gggtatctgg tacctgtggg      60
gacattgtga tgacccagac tccatcctcc caggctgtgt cagcagggga gaaggtcact     120
atgagctgca agtccagtca gagtctttta tacagtgaaa acaaaaagaa ctacttggcc     180
tggtaccagc agaaaccagg gcagtctcct aaactgctga tctactgggc atccactagg     240
gaatctgggg tccctgatcg cttcataggc agtggatctg gacagattt cactctgacc      300 atcagcagtg tgcaggcaga agacctggct gtttattact gccagcagta ctataacttt     360
ccgctcacgt tcggttctgg gaccaagctg gagatcaaa                            399

<210> SEQ ID NO 39
<211> LENGTH: 411
<212> TYPE: DNA
<213> ORGANISM: artificial
<220> FEATURE:
<223> OTHER INFORMATION: H7-9 IgH V region nt

<400> SEQUENCE: 39
atggctgtcc tggtgctgtt gctctgcctg gtgacatttc caagctgtgt cctgtcccaa      60
gtgcagctga aggagtcagg acctggtctg gtgcagccct cacagaccct gtccctcacc     120
tgcactgtct ctgggttctc attaaccagc tatactgtaa gctgggttcg ccagcctcca     180
ggaaagggtc tggagtggat tgcagcaata tcaagtggtg aaacacata ttctaattca      240 gctctcaaat cacgactgag catcagcagg gacacctcca agagccaatt tttcttaaaa     300
atgaacagtc tgcaaactga agacacagcc atgtacttct gtgccagaga gggatactat     360
gggtataact tgattactg gggccaagga gtcatggtca cagtctcctc a               411

<210> SEQ ID NO 40
<211> LENGTH: 381
<212> TYPE: DNA
<213> ORGANISM: artificial
<220> FEATURE:
<223> OTHER INFORMATION: H7-9 Igkappa V region nt

<400> SEQUENCE: 40
atggagtcac atactagggt cttcatattc ctgctgctct ggttgtctgg tgctgatggg      60
gacattgtga tgactcagtc tcccacatcc atgtccatat cagtaggaga cagggtcacc     120
atgaactgca aggccagtca aaatgtgggt tctaatgtag actggtacca acagaaaaca     180
gggcagtctc ctaaactgct tatctacaaa gcatccaacc ggtacacggg agtccctgat     240
cgcttcacag gcagtggatc tggaacagat ttcactttca ccatcagcaa catgcaggct     300
gaagacctgg ctgtttatta ctgtatgcag tctaactcct atccgctcac gttcggttct     360
gggaccaagc tggagatcaa a                                               381

<210> SEQ ID NO 41
<211> LENGTH: 417
<212> TYPE: DNA
<213> ORGANISM: artificial
<220> FEATURE:
<223> OTHER INFORMATION: G11-6 IgH V region nt

<400> SEQUENCE: 41
```

```
atggacacca ggctcagctt ggttttcctt gtccttttca taaaaggtgt ccagtgtgag    60
gtgcagctgg tggagtctgg gggaggctta gtgcagcctg gaaggtccct gaaactctcc   120
tgtgcagcct caggattcac tttcagtgac tattcatgg cctgggtccg ccaggctcca    180
aagaagggtc tggagtgggt cgcatccatt agttatgagg atagtagcac ttactatgga   240
gactccgtga agggccgatt cactatctcc agagataatg caaaaagcac cctatacctg   300
caaatgaaca gtctgaggtc tgaggacacg gccacttatt attgtgcaag aagtgcttgg   360
aactacccct attggtttgc ttactggggc caaggcactc tggtcactgt ctcttca      417
```

<210> SEQ ID NO 42
<211> LENGTH: 381
<212> TYPE: DNA
<213> ORGANISM: artificial
<220> FEATURE:
<223> OTHER INFORMATION: G11-6 Igkappa V region nt

<400> SEQUENCE: 42

```
atggagtcat atactcgggt cttcatattc ctgctgctct ggttgtctgg tgcagatggg    60
aacacagtga tgactcagtc tcccacatcc atgttcatat cagtaggaga cagggtcacc   120
gtgaactgca aggccagtca gaatgtgggt actaatgtag actggtacca acagaaaaca   180
ggtcagtctc ctaaactgct tatctatggg gcatccaacc ggtacactgg agtccctgat   240
cgcttcacag gcagtggatc tgggacagat ttcactctca ccatcagcaa catgcaggct   300
gaagacctgg ctgtttatta ctgtctacag tataactaca tccgtggac gttcggtgga   360 ggcaccaagc tggaattgaa a                                             381
```

<210> SEQ ID NO 43
<211> LENGTH: 19
<212> TYPE: DNA
<213> ORGANISM: artificial
<220> FEATURE:
<223> OTHER INFORMATION: YTM1142 primer

<400> SEQUENCE: 43

```
cctttccgct cacacctct                                                 19
```

<210> SEQ ID NO 44
<211> LENGTH: 19
<212> TYPE: DNA
<213> ORGANISM: artificial
<220> FEATURE:
<223> OTHER INFORMATION: YTM1143 primer

<400> SEQUENCE: 44

```
ggctcctggt ggacagtct                                                 19
```

<210> SEQ ID NO 45
<211> LENGTH: 19
<212> TYPE: DNA
<213> ORGANISM: artificial
<220> FEATURE:
<223> OTHER INFORMATION: YTM1144 primer

<400> SEQUENCE: 45

```
cggtggtcac ttcagaacg                                                 19
```

<210> SEQ ID NO 46
<211> LENGTH: 20
<212> TYPE: DNA

```
<213> ORGANISM: artificial
<220> FEATURE:
<223> OTHER INFORMATION: YTM1145 primer

<400> SEQUENCE: 46
tgctgaactc aaaccacagg                                                      20

<210> SEQ ID NO 47
<211> LENGTH: 16
<212> TYPE: DNA
<213> ORGANISM: artificial
<220> FEATURE:
<223> OTHER INFORMATION: M13(-20) primer

<400> SEQUENCE: 47
gtaaaacgac ggccag                                                          16

<210> SEQ ID NO 48
<211> LENGTH: 17
<212> TYPE: DNA
<213> ORGANISM: artificial
<220> FEATURE:
<223> OTHER INFORMATION: M13 reverse primer

<400> SEQUENCE: 48
caggaaacag ctatgac                                                         17

<210> SEQ ID NO 49
<211> LENGTH: 864
<212> TYPE: DNA
<213> ORGANISM: artificial
<220> FEATURE:
<223> OTHER INFORMATION: cPD1 nt

<400> SEQUENCE: 49
atggggagcc ggcgggggcc ctggccgctc gtctgggccg tgctgcagct gggctggtgg          60
ccaggatggc tcctagactc ccctgacagg ccctggagcc cgctcacctt ctccccggcg         120
cagctcacgg tgcaggaggg agagaacgcc acgttcacct gcagcctggc cgacatcccc         180
gacagcttcg tgctcaactg gtaccgcctg agccccgca accagacgga caagctggcc          240
gccttccagg aggaccgcat cgagccgggc cgggacaggc gcttccgcgt cacgcggctg         300
cccaacgggc gggacttcca catgagcatc gtcgctgcgc cctcaacga cagcggcatc          360 tacctgtgcg gggccatcta cctgccccc aacacacaga tcaacgagag tccccgcgca          420
gagctctccg tgacggagag aaccctggag ccccccacac agagcccag ccccccaccc          480 agactcagcg ccagttgca ggggctggtc atcggcgtca cgagcgtgct ggtgggtgtc          540
ctgctactgc tgctgctgac ctgggtcctg gccgctgtct tccccagggc cacccgaggt         600
gcctgtgtgt gcgggagcga ggacgagcct ctgaaggagg ccccgatgc agcgcccgtc          660 ttcaccctgg actacgggga gctggacttc cagtggcgag agaagacgcc ggagcccccg         720
gcgccctgtg ccccggagca gaccgagtat gccaccatcg tcttcccggg caggccggcg         780
tccccgggcc gcagggcctc ggccagcagc ctgcagggag cccagcctcc gagccccgag         840
gacggacccg gcctgtggcc cccc                                                864

<210> SEQ ID NO 50
<211> LENGTH: 867
<212> TYPE: DNA
<213> ORGANISM: artificial
<220> FEATURE:
<223> OTHER INFORMATION: cPLD1 nt
```

<400> SEQUENCE: 50

```
atgagaatgt ttagtgtctt tacattcatg gcctactgcc atttgctaaa agcatttacg      60
atcacagttt ctaaggacct gtatgtggta gagtatggtg gcaatgtgac aatggaatgc     120
aaattcccgg tggaaaaaca gttaaacttg tttgcactaa tcgtctactg ggaaatggag     180
gataaaaaaa ttatacaatt tgtgaatgga aggaagacc tgaaagttca gcacagcagc     240
tacagccaga gggctcagct attgaaggac cagctcttct tggggaaggc tgcgcttcag     300
atcacagatg tgagattgca ggatgcaggg gtttactgct gcttgatcgg ctatggcggt     360
gctgactaca agcggattac tttgaaagtt catgccccgt accgcaacat cagccaaaga     420
atttctgtgg atcctgtcac ctctgaacat gaactaatgt gtcaggctga gggttaccct     480
gaggctgaag tcatctggac aagcagtgac caccgagtcc tgagtggcaa aaccaccatc     540
actaattcca atagggaaga gaagcttttc aatgtgacca gcacgctgaa catcaatgca     600
acagctaatg agatttttcta ctgcactttt caaagatcag gtcctgagga aaacaatact     660
gccgagttgg tcatcccaga acgactgccc gttccagcaa gtgagaggac tcatttcatg     720
attctgggac ctttcctgtt gcttcttggt gtagtcctgg cagtcacttt ctgtctaaaa     780
aaacatggga gaatgatgga tgtggaaaaa tgttgcaccc gagataggaa ctcaaagaaa     840
cgaaatgata tacaatttga agagaca                                         867
```

<210> SEQ ID NO 51
<211> LENGTH: 39
<212> TYPE: DNA
<213> ORGANISM: artificial
<220> FEATURE:
<223> OTHER INFORMATION: YTM1167 primer

<400> SEQUENCE: 51

```
gtcgatgtca tgatctttat aatcaggggg ccacaggcc                             39
```

<210> SEQ ID NO 52
<211> LENGTH: 39
<212> TYPE: DNA
<213> ORGANISM: artificial
<220> FEATURE:
<223> OTHER INFORMATION: YTM1168 primer

<400> SEQUENCE: 52

```
gtcgatgtca tgatctttat aatctgtctc ttcaaattg                             39
```

<210> SEQ ID NO 53
<211> LENGTH: 36
<212> TYPE: DNA
<213> ORGANISM: artificial
<220> FEATURE:
<223> OTHER INFORMATION: YTM838 primer

<400> SEQUENCE: 53

```
gtcgatgtca tgatctttat aatcgtcgat gtcatg                                36
```

<210> SEQ ID NO 54
<211> LENGTH: 20
<212> TYPE: DNA
<213> ORGANISM: artificial
<220> FEATURE:
<223> OTHER INFORMATION: YTM1150 primer

<400> SEQUENCE: 54

```
gggcattcca gaaagatgag                                          20

<210> SEQ ID NO 55
<211> LENGTH: 20
<212> TYPE: DNA
<213> ORGANISM: artificial
<220> FEATURE:
<223> OTHER INFORMATION: YTM1151 primer

<400> SEQUENCE: 55
cccattcctt cctcttgtca                                          20

<210> SEQ ID NO 56
<211> LENGTH: 19
<212> TYPE: DNA
<213> ORGANISM: artificial
<220> FEATURE:
<223> OTHER INFORMATION: YTM1153 primer

<400> SEQUENCE: 56
actagactcc cctgacagg                                           19

<210> SEQ ID NO 57
<211> LENGTH: 23
<212> TYPE: DNA
<213> ORGANISM: artificial
<220> FEATURE:
<223> OTHER INFORMATION: YTM1154 primer

<400> SEQUENCE: 57
cgggatccct gcaactggcc gct                                      23

<210> SEQ ID NO 58
<211> LENGTH: 19
<212> TYPE: DNA
<213> ORGANISM: artificial
<220> FEATURE:
<223> OTHER INFORMATION: YTM1157 primer

<400> SEQUENCE: 58
atttactgtc acggttccc                                           19

<210> SEQ ID NO 59
<211> LENGTH: 26
<212> TYPE: DNA
<213> ORGANISM: artificial
<220> FEATURE:
<223> OTHER INFORMATION: YTM1158 primer

<400> SEQUENCE: 59
cgagatctag tcctttcatt tggagg                                   26

<210> SEQ ID NO 60
<211> LENGTH: 23
<212> TYPE: DNA
<213> ORGANISM: artificial
<220> FEATURE:
<223> OTHER INFORMATION: YTM171 primer

<400> SEQUENCE: 60
tgccatcaat cttccacttg aca                                      23

<210> SEQ ID NO 61
<211> LENGTH: 20
<212> TYPE: DNA
<213> ORGANISM: artificial
```

```
<220> FEATURE:
<223> OTHER INFORMATION: YTM172 primer

<400> SEQUENCE: 61
aaytttcttg tccaccttgg                                          20

<210> SEQ ID NO 62
<211> LENGTH: 36
<212> TYPE: DNA
<213> ORGANISM: artificial
<220> FEATURE:
<223> OTHER INFORMATION: YTM166 primer

<400> SEQUENCE: 62
ggccacgcgt cgactagtac gggggggggg gggggg                        36

<210> SEQ ID NO 63
<211> LENGTH: 17
<212> TYPE: DNA
<213> ORGANISM: artificial
<220> FEATURE:
<223> OTHER INFORMATION: YTM170 primer

<400> SEQUENCE: 63
ggccacgcgt cgactac                                             17

<210> SEQ ID NO 64
<211> LENGTH: 28
<212> TYPE: DNA
<213> ORGANISM: artificial
<220> FEATURE:
<223> OTHER INFORMATION: YTM173 primer

<400> SEQUENCE: 64
gttgttcawg argcacacga ctgaggca                                 28

<210> SEQ ID NO 65
<211> LENGTH: 20
<212> TYPE: DNA
<213> ORGANISM: artificial
<220> FEATURE:
<223> OTHER INFORMATION: YTM174 primer

<400> SEQUENCE: 65 aatagcccttt gaccaggcat                                         20

<210> SEQ ID NO 66
<211> LENGTH: 21
<212> TYPE: DNA
<213> ORGANISM: artificial
<220> FEATURE:
<223> OTHER INFORMATION: YTM1224 primer

<400> SEQUENCE: 66
aggatgatgt cttatgaaca a                                        21
```

ANTI-CANINE PD-1 ANTIBODY OR ANTI-CANINE PD-L1 ANTIBODY

TECHNICAL FIELD

The present invention relates to an anti-canine PD-1 antibody or an anti-canine PD-L1 antibody, an agent for inhibiting binding between a canine PD-1 and a canine PD-L1 containing such an antibody, a method for inhibiting binding between a canine PD-1 and a canine PD-L1 comprising using such an antibody, and a gene encoding such an antibody.

REFERENCE TO SEQUENCE LISTING

The official copy of the Sequence Listing is submitted concurrently with the specification as an ASCII formatted text file via EFS-Web, with a file name of "07375_001US_SEQListing.txt", a creation date of Dec. 5, 2016, and a size of 31,326 bytes. The Sequence Listing filed via EFS-Web is part of the specification and is incorporated in its entirety by reference herein.

BACKGROUND ART

In human, antibody medicines targeting immune checkpoint molecules, which are immunosuppressive molecules has lately drawn attention and many clinical trials thereof have been conducted. In particular, clinical trials for human cancer that target PD-1 (Programmed cell death 1) and PD-L1 (programmed cell death 1 ligand-1) have achieved excellent results and drawn attention as a next-generation cancer therapy (see non-Patent Documents 1 and 2).

PD-1 is a receptor on the surface of T cells. It has the function of suppressing activation of T cells and shown to have the function of suppressing the immune response against the self, etc. Such suppression of the immune response is achieved by binding of PD-L1, a ligand of PD-1, to PD-1. Cancer cells express PD-L1 and gain the ability to suppress the activation of T cells and evade immune response by binding of expressed PD-L1 to PD-1. Therefore, inhibiting binding between PD-1 and PD-L1 is considered to be effective in treating cancer.

So far, a cancer therapeutic agent comprising an anti-PD-L1 antibody as an active ingredient and having the effect of suppressing the proliferation of cancer cells in vivo (see Patent Document 1) and an anticancer agent comprising an anti-PD-1 antibody or an anti-PD-L1 antibody, functioning to restore the responsiveness of iNKT cells in which allergy has been induced by administration with an iNKT cell ligand (see Patent Document 2) have been proposed. Moreover, the development of anti-PD-1 antibodies as therapeutic agents for melanoma, non-small cell lung cancer, and renal cell cancer is in progress (see Non Patent Document 3).

The number of cancer cases of pets has been rapidly increased in these days due to the longevity of pets. Cancer therapies for pets, as well as those for humans, have progressed and the three major therapies of surgical, radiation, and chemical (anticancer agent) therapies have been performed positively.

In Japan, dogs are the most common household pets and approximately 13 million dogs are kept. Therefore, the number of cancer cases in dogs is increasing. For treating cancer of dogs, the aforementioned three major therapies employed conventionally have a limit and therapies targeting an immune checkpoint molecule such as PD-1 or PD-L1 are expected to be a new therapy that can be used instead of or along with the three major therapies. However, there has been a problem that antibody medicines for human PD-1 and PD-L1 are not effective in dogs. The development of antibodies against canine PD-1 and canine PD-L1 has been therefore demanded. However, studies on PD-1 and PD-L1 in dogs had not progressed: the expression of PD-1 and PD-L1 cDNAs in dogs was not confirmed and the production of antibodies recognizing canine PD-1 and PD-L1 was difficult.

PRIOR ART DOCUMENTS

Patent Documents

Patent Document 1
Japanese unexamined Patent Application Publication No. 2014-65748
Patent Document 2
Japanese unexamined Patent Application Publication No. 2010-83863

Non-Patent Documents

Non Patent Document 1
YOKOYAMA, Isao, "Activated development of antibody medicines related to PD-1 (in Japanese)" Mar. 6, 2013, Nikkei Medical online, Internet URL: http://medical.nikkeibp.co.jp/leaf/all/search/cancer/news/201303/529345.html (searched in Jun. 23, 2014)
Non Patent Document 2
NONAKA, Nozomi, "Marked and sustained tumor response with combination of ipilimumab and anti-PD-1 antibody medicine nivolumab in half of advanced malignant melanoma (in Japanese)" May 17, 2013, Nikkei Medical online, Internet URL: http://medical.nikkeibp.co.jp/leaf/all/search/cancer/news/2013 05/530569.html (searched in Jun. 23, 2014)
Non Patent Document 3
Suzanne L. et al., The New England Journal of Medicine Vol. 366, No. 26: 2443-2454, 2012

SUMMARY OF THE INVENTION

Object to be Solved by the Invention

Objects of the present invention are to provide an anti-canine PD-1 antibody or an anti-canine PD-L1 antibody, an agent for inhibiting binding between a canine PD-1 and a canine PD-L1 containing such an antibody, a method for inhibiting binding between a canine PD-1 and a canine PD-L1 comprising using such an antibody, and a gene encoding such an antibody.

Means to Solve the Object

The inventors first succeeded in cloning of cDNAs of canine PD-1 and canine PD-L1 and determined their nucleotide and amino acid sequences. Canine PD-1 or canine PD-L1 expressing cell lines were then produced using the canine PD-1 or canine PD-L1 cDNA. The inventors then succeeded in producing rat monoclonal antibodies against canine PD-1 or canine PD-L1 using the cell lines. Furthermore, the inventors have found that the obtained rat monoclonal antibodies have the ability to inhibit binding between canine PD-1 and canine PD-L1, thereby completing the present invention.

Accordingly, the present invention is as disclosed in the following:

(1) An anti-canine PD-1 antibody that specifically binds to a canine PD-1 consisting of the amino acid sequence set forth in SEQ ID NO: 1, described in the following (a) or (b):
(a) an anti-canine PD-1 antibody comprising: a heavy chain variable region having the amino acid sequence set forth in SEQ ID NO: 2 or an amino acid sequence having an identity of 90% or more with the amino acid sequence set forth in SEQ ID NO: 2; and a light chain variable region having the amino acid sequence set forth in SEQ ID NO: 3 or an amino acid sequence having an identity of 90% or more with the amino acid sequence set forth in SEQ ID NO: 3;
(b) an anti-canine PD-1 antibody comprising: a heavy chain variable region having the amino acid sequence set forth in SEQ ID NO: 4 or an amino acid sequence having an identity of 90% or more with the amino acid sequence set forth in SEQ ID NO: 4; and a light chain variable region having the amino acid sequence set forth in SEQ ID NO: 5 or an amino acid sequence having an identity of 90% or more with the amino acid sequence set forth in SEQ ID NO: 5.
(2) An anti-canine PD-L1 antibody that specifically binds to a canine PD-L1 consisting of the amino acid sequence set forth in SEQ ID NO: 6, described in the following (c) or (d):
(c) an anti-canine PD-L1 antibody comprising: a heavy chain variable region having the amino acid sequence set forth in SEQ ID NO: 7 or an amino acid sequence having an identity of 90% or more with the amino acid sequence set forth in SEQ ID NO: 7; and a light chain variable region having the amino acid sequence set forth in SEQ ID NO: 8 or an amino acid sequence having an identity of 90% or more with the amino acid sequence set forth in SEQ ID NO: 8;
(d) an anti-canine PD-L1 antibody comprising: a heavy chain variable region having the amino acid sequence set forth in SEQ ID NO: 9 or an amino acid sequence having an identity of 90% or more with the amino acid sequence set forth in SEQ ID NO: 9; and a light chain variable region having the amino acid sequence set forth in SEQ ID NO: 10 or an amino acid sequence having an identity of 90% or more with the amino acid sequence set forth in SEQ ID NO: 10.
(3) An anti-canine PD-1 antibody that specifically binds to a canine PD-1 consisting of the amino acid sequence set forth in SEQ ID NO: 1, described in the following (e) or (f):
(e) an anti-canine PD-1 antibody comprising: a heavy chain variable region comprising a CDR1 consisting the an amino acid sequence set forth in SEQ ID NO: 11, a CDR2 consisting of the amino acid sequence set forth in SEQ ID NO: 12, and a CDR3 consisting of the amino acid sequence set forth in SEQ ID NO: 13; and a light chain variable region comprising a CDR1 consisting of the amino acid sequence set forth in SEQ ID NO: 14, a CDR2 consisting of the amino acid sequence set forth in SEQ ID NO: 15, and a CDR3 consisting of the amino acid sequence set forth in SEQ ID NO: 16;
(f) an anti-canine PD-1 antibody comprising: a heavy chain variable region comprising a CDR1 consisting of the amino acid sequence set forth in SEQ ID NO: 17, a CDR2 consisting of the amino acid sequence set forth in SEQ ID NO: 18, and a CDR3 consisting of the amino acid sequence set forth in SEQ ID NO: 19; and a light chain variable region comprising a CDR1 consisting of the amino acid sequence set forth in SEQ ID NO: 20, a CDR2 consisting of the amino acid sequence set forth in SEQ ID NO: 21, and a CDR3 consisting of the amino acid sequence set forth in SEQ ID NO: 22.

(4) An anti-canine PD-L1 antibody that specifically binds to a canine PD-L1 consisting of the amino acid sequence set forth in SEQ ID NO: 6, described in the following (g) or (h):
(g) an anti-canine PD-L1 antibody comprising: a heavy chain variable region comprising a CDR1 consisting of the amino acid sequence set forth in SEQ ID NO: 23, a CDR2 consisting of the amino acid sequence set forth in SEQ ID NO: 24, and a CDR3 consisting of the amino acid sequence set forth in SEQ ID NO: 25; and a light chain variable region comprising a CDR1 consisting of the amino acid sequence set forth in SEQ ID NO: 26, a CDR2 consisting of the amino acid sequence set forth in SEQ ID NO: 27, and a CDR3 consisting of the amino acid sequence set forth in SEQ ID NO: 28;
(h) an anti-canine PD-L1 antibody comprising: a heavy chain variable region comprising a CDR1 consisting of the amino acid sequence set forth in SEQ ID NO: 29, a CDR2 consisting of the amino acid sequence set forth in SEQ ID NO: 30, and a CDR3 consisting of the amino acid sequence set forth in SEQ ID NO: 31; and a light chain variable region comprising a CDR1 consisting of the amino acid sequence set forth in SEQ ID NO: 32, a CDR2 consisting of the amino acid sequence set forth in SEQ ID NO: 33, and a CDR3 consisting of the amino acid sequence set forth in SEQ ID NO: 34.
(5) An agent for inhibiting binding between a canine PD-1 and a canine PD-L1 containing the antibody according to any one of (1) to (4) above.
(6) A method for inhibiting binding between a canine PD-1 and a canine PD-L1 comprising using the antibody according to any one of (1) to (4) above.
(7) A gene encoding the antibody according to any one of (1) to (4) above.

Effect of the Invention

Antibodies according to the present invention can recognize and bind to canine PD-1 or canine PD-L1 and can be therefore used in expression and functional analyses of canine PD-1 or canine PD-L1 and as an agent for inhibiting binding between canine PD-1 and canine PD-L1.

BRIEF DESCRIPTION OF DRAWINGS

FIG. 1 illustrates the nucleotide sequence of canine PD-1 (hereinafter, also referred to as "cPD1") and the amino acid sequence that the nucleotide sequence encodes.

FIG. 2 illustrates the nucleotide sequence of canine PD-L1 (hereinafter, also referred to as "cPDL1") and the amino acid sequence that the nucleotide sequence encodes.

FIG. 3 (A) illustrates results of examination of binding between rat monoclonal antibodies against cPD1 and NRK/cPD1. FIG. 3 (B) illustrates results of examination of binding between rat monoclonal antibodies against cPDL1 and NRK/cPDL1.

FIG. 4 (A) illustrates a result of examination of binding between human PD-L1 (hPDL1)-hIg and NRK/cPD1. Figure (B) illustrates a result of examination of binding between cPD1-hIg and NRK/cPDL1.

FIG. 5 (A) illustrates results of examination of inhibition of binding between hPDL1-hIg and NRK/cPD1 by rat monoclonal antibodies against cPD1. FIG. 5 (B) illustrates results of examination of inhibition of binding between cPD1-hIg and NRK/cPDL1 by rat monoclonal antibodies against cPDL1.

FIG. 6 illustrates results of examination of inhibition of binding between cPD1-hIg and NRK/cPDL1 by rat monoclonal antibodies against cPD1.

FIG. 7 illustrates results of adding a rat monoclonal antibody against PD-1 (anti-PD-1: 4F12-E6 or a rat monoclonal antibody against cPD-L1 (anti-PD-L1: G11-6) to peripheral blood mononuclear cells; further adding concanavalin A (ConA) for stimulated culturing; and measuring canine IFN-γ in the obtained culture supernatant by ELISA.

FIG. 8 illustrates results of culturing canine PBMCs in the presence of PMA/ionomycin or ConA; collecting the PBMCs; then analyzing PD-1 and PD-L1 expression in a CD3-positive fraction (T cells) by flow cytometry using a rat monoclonal antibody against cPD1 (4F12-E6) or a rat monoclonal antibody against cPDL1 (G11-6).

FIG. 9 illustrates results of culturing CD14-positive monocytes separated from canine PBMCs using magnetic beads in the presence of IL-4 and GM-CSF for 6 days to induce immature dendritic cells; and analyzing PD-1 or PD-L1 expression in the immature dendritic cells (MHC Class II antibody positive) by flow cytometry using a rat monoclonal antibody against cPD1 (4F12-E6) or a rat monoclonal antibody against cPDL1 (G11-6).

MODE OF CARRYING OUT THE INVENTION

An anti-canine PD-1 antibodies according to the present invention is not particularly limited as long as it is an anti-Canine PD-1 antibody that specifically binds to a canine PD-1 consisting of the amino acid sequence set forth in SEQ ID NO: 1, described in the following (a) or (b):
(a) an anti-canine PD-1 antibody comprising: a heavy chain variable region having the amino acid sequence set forth in SEQ ID NO: 2 or an amino acid sequence having an identity of 90% or more with the amino acid sequence set forth in SEQ ID NO: 2; and a light chain variable region having the amino acid sequence set forth in SEQ ID NO: 3 or an amino acid sequence having an identity of 90% or more with the amino acid sequence set forth in SEQ ID NO: 3;
(b) an anti-canine PD-1 antibody comprising: a heavy chain variable region having the amino acid sequence set forth in SEQ ID NO: 4 or an amino acid sequence having an identity of 90% or more with the amino acid sequence set forth in SEQ ID NO: 4; and a light chain variable region having the amino acid sequence set forth in SEQ ID NO: 5 or an amino acid sequence having an identity of 90% or more with the amino acid sequence set forth in SEQ ID NO: 5,
but it is preferred that the antibody is an anti-canine PD-1 antibody described in the following (a') or (b'):
(a') an anti-canine PD-1 antibody comprising: a heavy chain variable region consisting of the amino acid sequence set forth in SEQ ID NO: 2 or an amino acid sequence having an identity of 90% or more with the amino acid sequence set forth in SEQ ID NO: 2; and a light chain variable region consisting of the amino acid sequence set forth in SEQ ID NO: 3 or an amino acid sequence having an identity of 90% or more with the amino acid sequence set forth in SEQ ID NO: 3;
(b') an anti-canine PD-1 antibody comprising: a heavy chain variable region consisting of the amino acid sequence set forth in SEQ ID NO: 4 or an amino acid sequence having an identity of 90% or more with the amino acid sequence set forth in SEQ ID NO: 4; and a light chain variable region consisting of the amino acid sequence set forth in SEQ ID NO: 5 or an amino acid sequence having an identity of 90% or more with the amino acid sequence set forth in SEQ ID NO: 5. Such an anti-canine PD-1 antibody can recognize and bind to canine PD-1 and can be therefore used in expression and functional analyses of canine PD-1 and in inhibition of binding between canine PD-1 and canine PD-L1.

An anti-canine PD-L1 antibody according to the present invention is not particularly limited as long as it is an anti-canine PD-L1 antibody that specifically binds to a canine PD-L1 consisting of the amino acid sequence set forth in SEQ ID NO: 6, described in the following (c) or (d):
(c) an anti-canine PD-L1 antibody comprising: a heavy chain variable region having the amino acid sequence set forth in SEQ ID NO: 7 or an amino acid sequence having an identity of 90% or more with the amino acid sequence set forth in SEQ ID NO: 7; and a light chain variable region having the amino acid sequence set forth in SEQ ID NO: 8 or an amino acid sequence having an identity of 90% or more with the amino acid sequence set forth in SEQ ID NO: 8;
(d) an anti-canine PD-L1 antibody comprising: a heavy chain variable region having the amino acid sequence set forth in SEQ ID NO: 9 or an amino acid sequence having an identity of 90% or more with the amino acid sequence set forth in SEQ ID NO: 9; and a light chain variable region having the amino acid sequence set forth in SEQ ID NO: 10 or an amino acid sequence having an identity of 90% or more with the amino acid sequence set forth in SEQ ID NO: 10,
but it is preferred that it is an anti-canine PD-L1 antibody described in the following (c') or (d'):
(c') an anti-canine PD-L1 antibody comprising: a heavy chain variable region consisting of the amino acid sequence set forth in SEQ ID NO: 7 or an amino acid sequence having an identity of 90% or more with the amino acid sequence set forth in SEQ ID NO: 7; and a light chain variable region consisting of the amino acid sequence set forth in SEQ ID NO: 8 or an amino acid sequence having an identity of 90% or more with the amino acid sequence set forth in SEQ ID NO: 8;
(d') an anti-canine PD-L1 antibody comprising: a heavy chain variable region consisting of the amino acid sequence set forth in SEQ ID NO: 9 or an amino acid sequence having an identity of 90% or more with the amino acid sequence set forth in SEQ ID NO: 9; and a light chain variable region consisting of the amino acid sequence set forth in SEQ ID NO: 10 or an amino acid sequence having an identity of 90% or more with the amino acid sequence set forth in SEQ ID NO: 10. Such an anti-canine PD-L1 antibody can recognize and bind to canine PD-L1 and can be therefore used in expression and functional analyses of canine PD-L1 and in inhibition of binding between canine PD-1 and canine PD-L1.

Other aspects of the anti-canine PD-1 antibody according to the present invention include an anti-canine PD-1 antibody that specifically binds to a canine PD-1 consisting of the amino acid sequence set forth in SEQ ID NO: 1, described in the following (e) or (f):
(e) an anti-canine PD-1 antibody comprising: a heavy chain variable region comprising a CDR1 consisting of the amino acid sequence set forth in SEQ ID NO: 11, a CDR2 consisting of the amino acid sequence set forth in SEQ ID NO: 12, and a CDR3 consisting of the amino acid sequence set forth in SEQ ID NO: 13; and a light chain variable region comprising a CDR1 consisting of the amino acid sequence set forth in SEQ ID NO: 14, a CDR2 consisting of the amino acid sequence set forth in SEQ ID NO: 15, and a CDR3 consisting of the amino acid sequence set forth in SEQ ID NO: 16;

(f) an anti-canine PD-1 antibody comprising: a heavy chain variable region comprising a CDR1 consisting of the amino acid sequence set forth in SEQ ID NO: 17, a CDR2 consisting of the amino acid sequence set forth in SEQ ID NO: 18, and a CDR3 consisting of the amino acid sequence set forth in SEQ ID NO: 19; and a light chain variable region comprising a CDR1 consisting of the amino acid sequence set forth in SEQ ID NO: 20, a CDR2 consisting of the amino acid sequence set forth in SEQ ID NO: 21, and a CDR3 consisting of the amino acid sequence set forth in SEQ ID NO: 22.

Other aspects of the anti-canine PD-L1 antibody according to the present invention include an anti-canine PD-L1 antibody that specifically binds to a canine PD-L1 consisting of the amino acid sequence set forth in SEQ ID NO: 6, described in the following (g) or (h):

(g) an anti-canine PD-L1 antibody comprising: a heavy chain variable region comprising a CDR1 consisting of the amino acid sequence set forth in SEQ ID NO: 23, a CDR2 consisting of the amino acid sequence set forth in SEQ ID NO: 24, and a CDR3 consisting of the amino acid sequence set forth in SEQ ID NO: 25; and a light chain variable region comprising a CDR1 consisting of the amino acid sequence set forth in SEQ ID NO: 26, a CDR2 consisting of the amino acid sequence set forth in SEQ ID NO: 27, and a CDR3 consisting of the amino acid sequence set forth in SEQ ID NO: 28;

(h) an anti-canine PD-L1 antibody comprising: a heavy chain variable region comprising a CDR1 consisting of the amino acid sequence set forth in SEQ ID NO: 29, a CDR2 consisting of the amino acid sequence set forth in SEQ ID NO: 30, and a CDR3 consisting of the amino acid sequence set forth in SEQ ID NO: 31; and a light chain variable region comprising a CDR1 consisting of the amino acid sequence set forth in SEQ ID NO: 32, a CDR2 consisting of the amino acid sequence set forth in SEQ ID NO: 33, and a CDR3 consisting of the amino acid sequence set forth in SEQ ID NO: 34.

The type of the aforementioned anti-canine PD-1 and anti-canine PD-L1 antibodies (hereinafter, these are also collectively referred to as "the present anti-canine antibodies") is not particularly limited and includes a monoclonal antibody; a chimeric or caninized antibody produced as a recombinant protein from the sequence of a monoclonal antibody; and an antibody fragment consisting of a part(s) of antibody, such as F (ab')2, obtained by digesting antibody with pepsin, Fab, obtained by digesting antibody with papain, ScFv, in which a heavy chain variable region and a light chain variable region are connected by amino acid cross-linking, diabody, in which ScFvs are dimerized.

In the present invention, "an identity of 90% or more" means that the identity is 90% or more, preferably 93% or more, more preferably 95% or more, and further preferably 98% or more.

Examples of genes encoding the present anti-canine antibodies, for example, a gene encoding the aforementioned anti-canine PD-1 antibody include a gene comprising a gene encoding an amino acid sequence set forth in SEQ ID NO: 2 or an amino acid sequence having an identity of 90% or more with the amino acid sequence set forth in SEQ ID NO: 2 and a gene encoding an amino acid sequence set forth in SEQ ID NO: 3 or an amino acid sequence having an identity of 90% or more with the amino acid sequence set forth in SEQ ID NO: 3; wherein the antibody produced from the gene specifically binds to a canine PD-1 consisting of the amino acid sequence set forth in SEQ ID NO: 1. Specific examples include a gene comprising the nucleotide sequence set forth in SEQ ID NO: 35 and the nucleotide sequence set forth in SEQ ID NO: 36. Other examples include a gene comprising a gene encoding the amino acid sequences of CDR1-3 of the heavy chain variable region set forth in SEQ ID NOs: 11-13 and a gene encoding the amino acid sequences of CDR1-3 of the light chain variable region set forth in SEQ ID NOs: 14-16

Other aspects of the gene encoding the aforementioned anti-canine PD-1 antibody include a gene comprising a gene encoding the amino acid sequence set forth in SEQ ID NO: 4 or an amino acid sequence having an identity of 90% or more with the amino acid sequence set forth in SEQ ID NO: 4 and a gene encoding an amino acid sequence set forth in SEQ ID NO: 5 or an amino acid sequence having an identity of 90% or more with the amino acid sequence set forth in SEQ ID NO: 5; wherein the antibody produced from the gene specifically binds to a canine PD-1 consisting of the amino acid sequence set forth in SEQ ID NO: 1. Specific examples include a gene comprising the nucleotide sequence set forth in SEQ ID NO: 37 and the nucleotide sequence set forth in SEQ ID NO: 38. Other examples include a gene comprising a gene encoding the amino acid sequences of CDR1-3 of the heavy chain variable region set forth in SEQ ID NOs: 17-19 and a gene encoding the amino acid sequences of CDR1-3 of the light chain variable region set forth in SEQ ID NOs: 20-22

Examples of a gene encoding the aforementioned anti-canine PD-L1 antibody include a gene comprising a gene encoding an amino acid sequence set forth in SEQ ID NO: 7 or an amino acid sequence having an identity of 90% or more with the amino acid sequence set forth in SEQ ID NO: 7 and a gene encoding an amino acid sequence set forth in SEQ ID NO: 8 or an amino acid sequence having an identity of 90% or more with the amino acid sequence set forth in SEQ ID NO: 8; wherein the antibody produced from the gene specifically binds to a canine PD-L1 consisting of the amino acid sequence set forth in SEQ ID NO: 6. Specific examples include a gene comprising the nucleotide sequence set forth in SEQ ID NO: 39 and the nucleotide sequence set forth in SEQ ID NO: 40. Other examples include a gene comprising a gene encoding the amino acid sequences of CDR1-3 of the heavy chain variable region set forth in SEQ ID NOs: 23-25 and a gene encoding the amino acid sequences of CDR1-3 of the light chain variable region set forth in SEQ ID NOs: 26-28

Other aspects of the gene encoding the aforementioned anti-canine PD-L1 antibody include a gene comprising a gene encoding an amino acid sequence set forth in SEQ ID NO: 9 or an amino acid sequence having an identity of 90% or more with the amino acid sequence set forth in SEQ ID NO: 9 and a gene encoding an amino acid sequence set forth in SEQ ID NO: 10 or an amino acid sequence having an identity of 90% or more with the amino acid sequence set forth in SEQ ID NO: 10; wherein the antibody produced from the gene specifically binds to a canine PD-L1 consisting of the amino acid sequence set forth in SEQ ID NO: 6. Specific examples include a gene comprising the nucleotide sequence set forth in SEQ ID NO: 41 and the nucleotide sequence set forth in SEQ ID NO: 42. Other examples include a gene comprising a gene encoding the amino acid sequences of CDR1-3 of the heavy chain variable region set forth in SEQs ID NO: 29-31 and a gene encoding the amino acid sequences of CDR1-3 of the light chain variable region set forth in SEQ ID NOs: 32-34

An expression vector of a gene encoding the aforementioned anti-canine PD-1 antibody or anti-canine PD-L1 antibody can be produced by incorporating a gene encoding the aforementioned anti-canine PD-1 antibody or anti-canine PD-L1 antibody into a vector. The vector to be used as the expression vector is a vector capable of expressing a gene encoding the aforementioned anti-canine PD-1 or anti-canine PD-L1 antibody and can be a plasmid vector or a phage vector.

The aforementioned monoclonal antibody can be produced according to a conventional protocol. For example, it can be produced as a recombinant antibody by expressing a gene encoding one of the present anti-canine antibodies by the gene recombination technique. Methods for producing a recombination antibody include, for example, a method involving incorporating a gene encoding one of the present anti-canine antibodies into an expression vector; introducing the expression vector into host cells such as a mammalian cell line such as Chinese hamster ovary (CHO) cells, *Escherichia coli*, fungal cells, insect cells, and plant cells; and producing the recombinant antibody in the host cells (see Peter J. Delves, ANTIBODY PRODUCTION ESSENTIAL TECHNIQUES, WILEY, 1997). The nucleotide sequence of the gene encoding one of the present anti-canine antibodies to be incorporated into an expression vector can be optimized in codon sequence for the host cells to be used for the expression.

Moreover, a transgenic animal, such as a mouse, a cow, a goat, a sheep, a chicken, or a pig, in which a gene encoding one of the present anti-canine antibodies is incorporated can be created by a transgenic animal-creation technique and the antibody can be produced in a large amount in blood, milk, or the like of the transgenic animal.

Furthermore, the aforementioned monoclonal antibody can be produced by administering cells expressing a protein consisting of the amino acid sequence set forth in SEQ ID NO: 1 or 6 as an antigen to a non-human animal such as a mouse or a rat and screening for cellular clones that produce one of the present anti-canine antibodies by a cell fusion technique (the hybridoma technique (see Kohler G, et al., Nature 256: 495-497, 1975)), the trioma technique, the human B-cell hybridoma technique (see Danuta Kozbor, et al., Immunology Today 4, 72-79, 1983), and the EBV-hybridoma technique (see Cole et al., MONOCLONAL ANTIBODIES AND CANCER THERAPY: 77-96, Alan R. Liss, Inc., 1985)).

The aforementioned caninized antibody can be produced, for example, by replacing the constant regions of an antibody having heavy chain and light chain variable regions with constant regions of a canine antibody. The constant regions of the canine antibody can be those of known canine antibodies.

The produced present anti-canine antibody can be purified by Protein A or Protein G column chromatography, ion exchange chromatography, hydrophobic chromatography, ammonium sulfate precipitation, gel filtration, affinity chromatography, or the like.

An agent for inhibiting binding between a canine PD-1 and a canine PD-L1 containing one of the anti-canine antibodies is not particularly limited as long as it contains one of the present anti-canine antibodies and can comprise a plurality of types of anti-canine PD-1 and/or anti-canine PD-L1 antibodies. Such an agent for inhibiting binding inhibits binding between a canine PD-1 and a canine PD-L1 and can be therefore used as an agent for treating cancer in a dog expressing PD-L1. The inhibition of binding according to the present invention includes inhibition of binding both in vivo and in vitro.

The aforementioned agent for inhibiting binding can comprise a pharmaceutically acceptable additive usually used in the formulation, such as an excipient, a binder, a lubricant, a disintegrator, a preservative, a tonicity adjusting agent, a stabilizer, a dispersant, an antioxidant, a colorant, a flavor agent, or a buffer. The aforementioned agent for inhibiting binding can be administered into a dog in a mode of administration, such as the oral administration as well as the parenteral administration by injection or drip infusion, application, suppository, or intranasal spray, and can be formulated into any form as appropriate.

Examples of the amount of a present antibody comprised in the aforementioned agent for inhibiting binding include 0.0001-50% by weight and preferable examples include 0.001-5% by weight.

The method for inhibiting binding between a canine PD-1 and a canine PD-L1 comprising using one of the present anti-canine antibodies is not particularly limited as long as one of the present anti-canine antibodies is used and a plurality of types of anti-canine PD-1 and/or anti-canine PD-L1 antibodies can be used.

The present invention will be described more specifically with Examples below. However, the technical scope of the present invention is not limited to these illustrations.

Primers to be used in PCR in the following Examples are listed in Table 1.

TABLE 1

| Primer name | Nucleotide sequence (5' to 3') | SEQ ID No. | Direction | Purpose |
| --- | --- | --- | --- | --- |
| YTM1142 | CCTTTCCGCTCACACCTCT | 43 | F | to amplify the full length |
| YTM1143 | GGCTCCTGGTGGACAGTCT | 44 | R | of cPD1 |
| YTM1144 | CGGTGGTCACTTCAGAACG | 45 | F | to amplify the full length |
| YTM1145 | TGCTGAACTCAAACCACAGG | 46 | R | of cPDL1 |
| M13(-20) | GTAAAACGACGGCCAG | 47 | F | sequence reaction |
| M13 reverse | CAGGAAACAGCTATGAC | 48 | R | sequence reaction |
| YTM1167 | GTCGATGTCATGATCTTTATAATCAGGGGCCACAGGCC | 51 | R | Addition of 1st FLAG tag to cPD1 |
| YTM1168 | GTCGATGTCATATCTTTATAATCTGTCTCTTCAAATTG | 52 | R | Addition of 1st FLAG tag to cPDL1 |
| YTM838 | GTCGATGTCATGATCTTTATAATCGTCGATGTCATG | 53 | R | Addition of 2nd FLAG tag |
| YTM1150 | GGGCATTCCAGAAAGATGAG | 54 | F | to amplify the full length |
| YTM1151 | CCCATTCCTTCCTCTTGTCA | 55 | R | of hPDL1 |
| YTM1153 | ACTAGACTCCCCTGACAGG | 56 | F | to amplify the extracellular |

TABLE 1-continued

| Primer name | Nucleotide sequence (5' to 3') | SEQ ID No. | Direction | Purpose |
|---|---|---|---|---|
| YTM1154 | CGGGATCCCTGCAACTGGCCGCT | 57 | R | domain of cPD1 |
| YTM1157 | ATTTACTGTCACGGTTCCC | 58 | F | to amplify the extracellular |
| YTM1158 | CGAGATCTAGTCCTTTCATTTGGAGG | 59 | R | domain of hPDL1 |
| YTM166 | GGCCACGCGTCGACTAGTACGGGGGGGGGGGGGGG | 62 | F | to amplify the V region of |
| YTM170 | GGCCACGCGTCGACTAC | 63 | F | rat heavy and light chains |
| YTM171 | TGCCATCAATCTTCCACTTGACA | 60 | R | |
| YTM172 | AAYTTTCTTGTCCACCTTGG | 61 | R | |
| YTM173 | GTTGTTCAWGARGCACACGACTGAGGCA | 64 | R | |
| YTM174 | AATAGCCCTTGACCAGGCAT | 65 | R | |
| YTM1224 | AGGATGATGTCTTATGAACAA | 65 | R | |

F, forward; R, reverse; Bold types indicate restriction enzyme sites and underlines indicate FLAG coding region.

The NRK cells, a rat kidney cell line, and the HEK293T cells, a human kidney cell line, used in the following Examples were maintained in the DMEM medium supplemented with 10% FBS, 100 units/ml penicillin, 100 μg/ml streptomycin, and 55 μM 2-mercaptoethanol. These cell lines were used after culturing at a $CO_2$ gas concentration of 5%, and 37° C. in a humidified incubator.

EXAMPLES

Example 1

[Production of Rat Monoclonal Antibody Against cPD1 or cPDL1]
1. cDNA Cloning of cPD1 or cPDL1
(Designing of Primers)

The forward primer (YTM1142: SEQ ID NO: 43) and the reverse primer (YTM1143: SEQ ID NO: 44) for amplifying cDNA of cPD1 are designed based on the sequence of NCBI (http://www.ncbi.nlm.nih.gov/guide/) Accession No. XM_543338 and the forward primer (YTM1144: SEQ ID NO: 45) and the reverse primer (YTM1145: SEQ ID NO: 46) for amplifying cDNAs of cPDL1 were designed based on the sequence of NCBI Accession No. XM_005615936.1. None of the sequences of Accession No. XM_543338 and Accession No. XM_005615936.1 were found in the genes whose expression is confirmed in a dog.

(PCR Reaction)

cPD1 and cPDL1 genes were amplified using the aforementioned primer pairs, thymic cDNA in a normal dog as template, KOD-Plus-Neo (Toyobo Co. Ltd.), according to the attached protocol. The PCR was conducted with pre-denaturation at 94° C. for 2 minutes; then 35 cycles of denaturation at 98° C. for 10 seconds, annealing at 58° C. for 30 seconds, and extension 68° C. for 60 seconds; and a final extension at 68° C. for 10 minutes.

(Insertion into Vector and Nucleotide Sequencing)

The PCR products prepared as described above were gel-purified and inserted at the SmaI site in the pBluescript SK (−) vector to produce constructed vectors comprising cPD1 or cPDL1 gene as the insert (pBS-cPD1, pBS-cPDL1). The nucleotide sequences of the constructed vectors were determined using a forward primer (M13(−20): SEQ ID NO: 47) and a reverse primer (M13 reverse: SEQ ID NO: 48), BigDye (registered trademark) Termination v3.1 Cycle Sequencing Kit (Perkin-Elmer), and ABI Prism (registered trademark) 377 automatic DNA sequencer (Applied Biosystems). The nucleotide sequence of the obtained cPD1 and the amino acid sequence encoded by the nucleotide sequence are shown in FIG. 1. The nucleotide sequence of cPDL1 and the amino acid sequence encoded by the nucleotide sequence is shown in FIG. 2. The nucleotide sequence of cPD1 is shown SEQ ID NO: 49, the amino acid sequence thereof in SEQ ID NO: 1, the nucleotide sequence of cPDL1 in SEQ ID NO: 50, and the amino acid sequence thereof in SEQ ID NO: 6.

2. Production of Rat Monoclonal Antibody
(Construction of cPD1 or cPDL1 Expression Vector)

The retroviral vectors that overexpress cPD1 or cPDL1 protein were constructed. To add two FLAG tag sequences at the C-terminus of cPD1 and cPDL1 sequences, primary PCR was first conducted using pBS-cPD1 as template, a forward primer (YTM1142: SEQ ID NO: 43), and a reverse primer (YTM1167: SEQ ID NO: 51) comprising a FLAG tag sequence at the C-terminus of the cPD1 sequence for the amplification of cPD1, or pBS-cPDL1 as template, a forward primer (YTM1144: SEQ ID NO: 45), and a reverse primer (YTM1168: SEQ ID NO: 52) comprising a FLAG tag sequence at the C-terminus of the cPDL1 sequence for the amplification of cPDL1.

The second PCR was then conducted using each 1st PCR product as template, a forward primer same as that in the primary PCR, and a reverse primer (YTM838: SEQ ID NO: 53) comprising a double FLAG tag sequence that anneals with the 1st FLAG tag sequence. Each obtained PCR product was inserted at EcoRI and the NotI sites in the pMxs-IP vector to produce pMx-IP-cPD1-FL and pMx-IP-cPDL1-FL#9.

(Production of Transfected Cell)

NRK cells are transfected with pMx-IP-cPD1-FL or pMx-IP-cPDL1-FL#9 by a common transfection technique to produce the NRK cells that stability express cPD1 and the NRK cells that stability express cPDL1. NRK cells ($3.5 \times 10^5$ cells) were first plated in a 6 well dish 1 day before the transfection. The transfection of cells was conducted using Lipofectamine 2000 (Invitrogen) according to the attached protocol. Cells after the transfection were incubated for 48 hours and then cultured in the presence of 7.5 μg/ml puromycin (Sigma-Aldrich) to obtain stable transfected cells to produce the NRK cell that stability expressing cPD1 (NRK/cPD1) and the NRK cells stability expressing cPDL1 (NRK/cPDL1).

Stable expression of cPD1 and cPDL1 in the NRK/cPD1 and NRK/cPDL1 was confirmed by immunofluorescence using the anti-FLAG M2 antibody (1:1,000 dilution, Sigma-Aldrich) as the primary antibody and IgG-Dylight (registered trademark) 488-labelled anti-mouse (Biolegend) as the secondary antibody.

(Production of Rat Monoclonal Antibody)

To produce rat monoclonal antibodies against cPD1 or cPDL1, the NRK/cPD1 or NRK/cPDL1 (in 500 µl of the DMEM medium, 1×10$^7$ cells) produced as described above was emulsified with an equal amount of Titer Max (registered trademark) Gold (CytRx) and administered subcutaneously to the footpad of hindleg in 7 week-old Sprague-Dawley rat (Kudo Co. Ltd.). Lymph node cells in the pople were isolated 2 weeks after administration and fused with P3U1 cells. More specifically, lymph node monocytes (1×10$^8$ cells) and P3U1 cells (2×10$^7$ cells) were mixed and washed twice with the serum-free RPMI1640 medium. The supernatant was removed and cells were then incubated at 37° C. for 2 minutes. 0.5 ml of polyethyleneglycol 1500 (Roche Diagnostics) at 37° C. and then 9 ml of the serum-free RPMI1640 medium at 37° C. were added and the suspension was centrifuged at room temperature at 900 rpm for 5 minutes. The supernatant was removed and the cells were then suspended in 36 ml of the GIT medium (Wako Pure Chemical Industries) comprising 10% FBS and hypoxanthine-aminopterin-thymidine (HAT: Life Technologies) and cultured in a humidified incubator at $CO_2$ gas concentration of 5% and 37° C. for 1 hour. 4 ml of the BM-Condimed H1 medium (Roche Diagnostics) was added and the cells were plated and cultured in four 96 well tissue culture plates (100 µl/well). After culturing to obtain colonies, NRK cell-positive hybridomas expressing cPD1 or cPDL1 were identified by ELISA or flow cytometry and the hybridomas were cloned by limiting dilution. The hybridomas 3B7-D9 and 4F12-E6 were obtained as NRK cell-positive hybridomas expressing cPD1 and the hybridomas H7-9 and G11-6 as NRK cell-positive hybridomas expressing cPDL1. Hereinafter, the antibody produced by the hybridoma 3B7-D9 is also referred to as "3B7-D9," the antibody produced by the hybridoma 4F12-E6 as "4F12-E6," the antibody produced by the hybridoma H7-9 as "H7-9," and the antibody produced by the hybridoma G11-6 as "G11-6." The hybridomas 3B7-D9, 4F12-E6, H7-9, and G11-6 are kept in the Joint Faculty of Veterinary Medicine at Yamaguchi University and available under a certain condition.

Example 2

[Confirmation of Anti-cPD1 or Anti-cPDL1 Antibody]
(Antibody Concentration and Cell Number)

The binding between a rat monoclonal antibody against cPD1, 3B7-D9 or 4F12-E6, and NRK/cPD1 produced as described above and the binding of a rat monoclonal antibody against cPDL1, H7-9 or G11-6 and NRK/cPDL1 produced as described above were examined by the flow cytometry analysis described below. Concentrations of each rat monoclonal antibody were 0, 0.04, 0.156, 0.625, 2.5, and 10 µg/ml and NRK/cPD1 (2×10$^5$ cells) or NRK/cPDL1 (2×10$^5$ cells) were used.

(Flow Cytometry Analysis)

The staining of the cell lines to be used in the flow cytometry analysis was conducted according to the method described in the following documents (Mizuno et al., J Vet Med Sci, 71(12): 1561-1568, 2009). The respective purified rat monoclonal antibodies against cPD1 or cPDL1 were used as the primary antibodies and anti-rat IgG-PE (Southern biotech) was used as the secondary antibody. The samples were analyzed using BD AccuriC6 (BD Bioscience) and the obtained results were analyzed by FlowJo software (Treestar).

(Results)

The results are shown in FIG. 3. FIG. 3(A) illustrates results of the examination of binding between rat monoclonal antibodies against cPD1 (anti-cPD1 mAb) and NRK/cPD1 and FIG. 3(B) illustrates results of examination of binding between rat monoclonal antibodies against cPDL1 (anti-cPD-L1 mAb) and NRK/cPDL1. The abscissa indicates the fluorescence intensity of the fluorescent labeled secondary antibody against the produced antibody and the ordinate indicates the concentration of each rat monoclonal antibody. It was confirmed that any of the rat monoclonal antibodies increased the fluorescence intensity, the rat monoclonal antibodies against cPD1, 3B7-D9 and 4F12-E6 bound with NRK/cPD1, and the rat monoclonal antibodies against cPDL1, H7-9 and G11-6 bound with NRK/cPDL1, as shown in FIG. 3. Accordingly, it was demonstrated that 3B7-D9 and 4F12-E6 are anti-cPD1 antibodies and H7-9 and G11-6 are anti-cPDL1 antibodies.

Example 3

[Test of Inhibition of Binding Between PD-1 and PD-L1 with Rat Monoclonal Antibody]
1. Production of Fusion Protein Between cPD1 and Human IgFc Region and Fusion Protein Between Human PD-L1 (hPDL1) and Human IgFc Region
(Construction of hPDL1 Expression Plasmid)

To construct hPDL1 expression plasmid, hPDL1 was amplified using cDNA derived from the human Burkitt lymphoma cell line (Raji) as template, a forward primer (YTM1150: SEQ ID NO: 54) and a reverse primer (YTM1151: SEQ ID NO: 55). The amplification by the PCR was conducted in a way similar to that described for Example 1. The amplified PCR product was introduced at the SmaI site in the pBluescript SK (−) vector. This plasmid was digested with EcoRI and NotI, the obtained fragments were ligated at the EcoRI and NotI sites in the pMxs-IP vector to produce the hPDL1 expression plasmid, pMx-IP-hPDL1#21.

(Production of Fusion Protein-Expression Vector)

A vector expressing a fusion protein between the extracellular region of cPD1 or hPDL1 and a human IgG2 Fc region was constructed. To produce such an expression vector, the extracellular region of cPD1 was amplified by conducting PCR using pMx-IP-cPD1-FL produced in Example 1 as template, a forward primer (YTM1153: SEQ ID NO: 56), and a reverse primer (YTM1154: SEQ ID NO: 57). The extracellular region of hPDL1 was amplified by conducting PCR using pMx-IP-hPDL1#21 produced as described above as template, a forward primer (YTM1157: SEQ ID NO: 58), and a reverse primer (YTM1158: SEQ ID NO: 59). The PCR products cPD1 were respectively digested with BamHI for cPD1 and BglII for hPDL1 and cloned at the EcoRV and BglII sites in the pFUSE-hIgG2-Fc2 vector (Invivogen) to produce a vector expressing a fusion protein with the extracellular region of cPD1 and the human IgG2 Fc region (pFUSE-cPD1-hIg#2) and a vector expressing a fusion protein of the extracellular region of hPDL1 and the human IgG2 Fc region (pFUSE-hPDL1-hIg#9).

(Production and Purification of Fusion Protein)

The HEK293T cell line was transfected with the vector pFUSE-cPD1-hIg#2, pFUSE-hPDL1-hIg#9, produced as described above, or the empty vector pFUSE-hIgG2-Fc2. 2×10$^6$ HEK293T cells were first plated in four 10 cm dishes 1 day before the transfection. 7.5 µg of each vector and 375 µl of OPTI-MEM comprising 30 µl of 1 mg/ml PEI Max were then mixed and incubated at room temperature for 15 minutes, and added to the cells. 24 hours after the transfection, medium was replaced into the serum-free GIT medium (Wako Pure Chemical Industries) and the cells were further cultured for 48 hours. Supernatant was collected from each of the transfected cells on Day 4 and Day 8 and purified with rProtein A agarose (GE healthcare). Salts were then removed from the soluble protein by dialysis to produce the fusion protein of the extracellular region of cPD1 and the hIgG2 Fc region (cPD1-hIg) and the fusion protein of the extracellular region of hPDL1 and the hIgG2 Fc region (hPDL1-hIg). The purity of the fusion proteins was checked by SDS-PAGE and Western blotting.

2. Test of Binding Between PD-1 and PD-L1

As a preliminary examination of the tests of inhibition of PD-1 and PD-L1 with rat monoclonal antibodies described later, the binding between hPDL1-hIg and NRK/cPD1 or the binding between cPD1-hIg and NRK/cPDL1 was examined in a way similar to the aforementioned flow cytometry analysis. Concentrations of hPDL1-hIg and cPD1-hIg were 0, 0.04, 0.156, 0.625, 2.5, 10, and 40 µg/ml and NRK/cPD1 ($2 \times 10^5$ cells) or NRK/cPDL1 ($2 \times 10^5$ cells) was used. The results are shown in FIG. 4. FIG. 4(A) illustrates a result of examination of binding between hPDL1-hIg and NRK/cPD1 and FIG. 4(B) illustrates a result of examination of binding between cPD1-hIg and NRK/cPDL1. The abscissa indicates the fluorescence intensity of the fluorescent labeled secondary antibody produced against the fusion protein, and the ordinate indicates the concentration of hPDL1-hIg or cPD1-hIg. It was demonstrated that hPDL1-hIg binds to NRK/cPD1 and cPD1-hIg binds to NRK/cPDL1 as shown in FIG. 4.

3. Test of Inhibition of Binding Between PD-1 and PD-L1 with Rat Monoclonal Antibody
(Flow Cytometry Analysis)

The following (1) to (3) were examined: (1) whether the rat monoclonal antibodies against cPD1 inhibit binding between hPDL1-hIg and NRK/cPD1 by having NRK/cPD1 interacted with a rat monoclonal antibody against cPD1 (3B7-D9, 4F12-E6) and then having hPDL1-hIg interacted with them; (2) whether the rat monoclonal antibodies against cPDL1 inhibit binding between cPD1-hIg and NRK/cPDL1 by having NRK/cPDL1 interacted with a rat monoclonal antibody against cPDL1 (H7-9, G11-6) and then having cPD1-hIg interacted with them; or (3) Whether the rat monoclonal antibodies against cPD1 inhibit binding between cPD1-hIg and NRK/cPDL1 by having a rat monoclonal antibody against cPD1 (3B7-D9, 4F12-E6) interacted with cPD1-hIg and then having NRK/cPDL1 interacted with the mixed reactant. The inhibition of binding between PD-1 and PD-L1 with each antibody was examined in a way similar to the aforementioned flow cytometry analysis. Concentrations of each rat monoclonal antibody were 0, 0.04, 0.156, 0.625, 2.5, and 10 µg/ml, the concentration of hPDL1-hIg and cPD1-hIg was 40 µg/ml, and NRK/cPD1 ($2 \times 10^5$ cells) or NRK/cPDL1 ($2 \times 10^5$ cells) was used.

(Results)

The results are shown in FIGS. 5 and 6. FIG. 5(A) illustrates results of examination of inhibition of binding between hPDL1-hIg and NRK/cPD1 by rat monoclonal antibodies against cPD1; FIG. 5(B) illustrates results of examination of inhibition of binding between cPD1-hIg and NRK/cPDL1 by rat monoclonal antibodies against cPDL1; and FIG. 6 illustrates results of examination of inhibition of binding between cPD1-hIg and NRK/cPDL1 by rat monoclonal antibodies against cPD1. The abscissa indicates the fluorescence intensity of the fluorescent labeled secondary antibody against the produced antibody, the left ordinate indicates the concentration of each rat monoclonal antibody, and the right ordinate indicates the presence (+) or the absence (−) of hPDL1-hIg or cPD1-hIg. It was demonstrated that the rat monoclonal antibodies against cPD1, 3B7-D9, 4F12-E6 inhibit the binding between hPDL1-hIg and NRK/cPD1 and the binding between cPD1-hIg and NRK/cPDL1 and the rat monoclonal antibodies against cPDL1, H7-9 and G11-6 inhibit the binding between cPD1-hIg and NRK/cPDL1, as shown FIGS. 5(A), (B), and 6.

Example 4

[Determination of Nucleotide Sequences of Heavy Chain and Light Chain of Rat Monoclonal Antibody]

Total RNA was isolated from each hybridoma cell line obtained in Example 1. The nucleotide sequence of the immunoglobulin heavy chain (IgG2a) and the nucleotide sequence of the κ light chain comprising all variable regions and 5' region of the constant regions were obtained by the 5' RACE PCR technique.

The isolated RNA was first reverse-transcribed using the reverse transcriptase Superscript (registered trademark) III. As a primer, YTM171 (SEQ ID NO: 60) was used for the amplification of the light chain and YTM172 (SEQ ID NO: 61) for the amplification of the heavy chain. After the reverse transcription reaction, polyC was added by TdT enzymatic reaction and then the primary PCR was conducted using a forward primer (YTM166: SEQ ID NO: 62) and a reverse primer (YTM171: SEQ ID NO: 60) for the amplification of the light chain and a forward primer (YTM166: SEQ ID NO: 62) and a reverse primer (YTM172: SEQ ID NO: 61) for the amplification of the heavy chain. The PCR products were gel-purified and the nested PCR was conducted using a forward primer (YTM170: SEQ ID NO: 63) and a reverse primer (YTM173: SEQ ID NO: 64), or a forward primer (YTM170: SEQ ID NO: 63) and a reverse primer (YTM174: SEQ ID NO: 65) to amplify all variable regions of the light chain or the heavy chain. In hybridomas 3B7-D9 and G11-6, YTM1224 (SEQ ID NO: 42) was used, instead of YTM171 as a primer in 5' RACE and the primary PCR. The nested PCR products were cloned into the pBluescript SK (−) vector and their nucleotide sequences and the amino acid sequences encoded by the nucleotide sequence were determined.

The nucleotide sequence of the heavy chain variable region of 3B7-D9 is set forth in SEQ ID NO: 35, the amino acid sequence in SEQ ID NO: 2, the nucleotide sequence of the light chain variable region in SEQ ID NO: 36, and the amino acid sequence in SEQ ID NO: 3. The nucleotide sequence of the heavy chain variable region of 4F12-E6 is set forth in SEQ ID NO: 37, the amino acid sequence in SEQ ID NO: 4, the nucleotide sequence of the light chain variable region in SEQ ID NO: 38, and the amino acid sequence in SEQ ID NO: 5. The nucleotide sequence of the heavy chain variable region of H7-9 is set forth in SEQ ID NO: 39, the amino acid sequence in SEQ ID NO: 7, the nucleotide sequence of the light chain variable region in SEQ ID NO: 40, and the amino acid sequence in SEQ ID NO: 8. The nucleotide sequence of the heavy chain variable region of G11-6 is set forth in SEQ ID NO: 41, the amino acid sequence in SEQ ID NO: 9, the nucleotide sequence of the light chain variable region in SEQ ID NO: 42, and the amino acid sequence in SEQ ID NO: 10.

Furthermore, the amino acid sequences of CDRs of each heavy chain variable region and light chain variable region were identified by comparing the sequence with the amino acid sequences of known antibodies. The amino acid sequences of the CDR1-3 of the heavy chain variable region of 3B7-D9 are set forth in SEQ ID NOs: 11-13 and the amino acid sequences of the CDR1-3 of the light chain variable region in SEQ ID NOs: 14-16, respectively. The amino acid sequences of the CDR1-3 of the heavy chain variable region of 4F12-E6 are set forth in SEQ ID NOs: 17-19 and the amino acid sequences of the CDR1-3 of the light chain variable region in SEQ ID NOs: 20-22, respectively. The amino acid sequences of the CDR1-3 of the heavy chain variable region of H7-9 are set forth in SEQ ID NOs: 23-25 and the amino acid sequences of the CDR1-3 of the light chain variable region in SEQ ID NOs: 26-28, respectively. The amino acid sequences of the CDR1-3 of the heavy chain variable region of G11-6 are set forth in SEQ ID NOs: 29-31 and the amino acid sequences of the CDR1-3 of the light chain variable region in SEQ ID NOs: 32-34, respectively.

Example 5

[Enhancement of IFN-γ Production]

Peripheral blood mononuclear cells (PBMC) were collected from 3 dogs (A, B, and C), PBMCs were transferred into 96 well round bottom plates at 2×10$^5$ per well, isotype (rat IgG2a: eBioscience), a rat monoclonal antibody against PD-1 (anti-PD-1: 4F12-E6), or rat monoclonal antibody against cPDL1 (anti-PD-L1: G11-6) was added to a concentration of 10 μg/ml, and concanavalin A (ConA) was added to 5 μg/ml. The cells were cultured with stimulation for 3 days and canine IFN-γ in the obtained culture supernatant was measured by the canine IFN-gamma DuoSet ELISA (R & D). The results are shown in FIG. 7.

IFNγ produced by ConA stimulation exhibited a tendency of produced and enhanced in the presence of the anti-PD-1, 4F12-E6 and the anti-PD-L1, G11-6, as shown in FIG. 7. This suggested the possibility that expression of PD-1 and PD-L1 is enhanced by ConA stimulation in canine T cells and binding of the PD-L1 to the PD-1 prevents excessive activation of T cells and also suggested that the obtained PD-1 and PD-L1 antibodies can inhibit the interaction between PD-1 and PD-L1 molecules expressed on canine cells.

Example 6

[PD-1 or PD-L1 Expression Induced in the Presence of PMA (Phorbol-12-Myristate-13-Acetate)/Ionomycin (Iono) or ConA]

Canine PBMCs were cultured in the presence of PMA/ionomycin or ConA for 3 days, PBMCs were collected, and PD-1 and PD-L1 expression in a CD3-positive fraction (T cells) was then analyzed by flow cytometry using a rat monoclonal antibody against cPD1 (4F12-E6) or a rat monoclonal antibody against cPDL1 (G11-6). The results are shown in FIG. 8.

It was demonstrated that activated canine T cells are induced to express both PD-1 and PD-L1 expression, as shown in FIG. 8. It was shown that the PD-1 or PD-L1 expression in T cells can be thus examined by using an antibody according to the present invention and that, in other words, expression of PD-1 and/or PD-L1 expressed on the surface of canine cells can be examined.

Example 7

[Induction of PD-1 or PD-L1 Expression in the Presence of IL-4 or GM-CSF]

Immature dendritic cells were induced by culturing CD14-positive monocytes separated from canine PBMCs using magnetic beads in the presence of IL-4 and GM-CSF for 6 days. The cells were confirmed to be immature dendritic cells by the simultaneous staining of MHC Class II antibodies (eBioscience). FIG. 9 illustrates results of analyzing PD-1 and PD-L1 expression in the obtained immature dendritic cells by flow cytometry using a rat monoclonal antibody against cPD1 (4F12-E6) or a rat monoclonal antibody against cPDL1 (G11-6).

It was confirmed that PD-1 is not expressed, but PDL-1 is expressed, as shown in FIG. 9. It was demonstrated that PD-1 or PD-L1 expression in immature dendritic cells can be thus examined using an antibody according to the present invention.

INDUSTRIAL APPLICABILITY

Rat monoclonal antibodies obtained according to the present invention can recognize and bind to canine PD-1 or canine PD-L1 and be therefore used in expression and functional analyses of canine PD-1 or canine PD-L1 and as an agent for inhibiting binding between canine PD-1 and canine PD-L1.

The invention claimed is:

1. An anti-canine PD-1 antibody that specifically binds to a canine PD-1 consisting of the amino acid sequence set forth in SEQ ID NO: 1,
said antibody comprising:
(a) a heavy chain variable region comprising a CDR1 consisting of the amino acid sequence set forth in SEQ ID NO: 11, a CDR2 consisting of the amino acid sequence set forth in SEQ ID NO: 12, and a CDR3 consisting of the amino acid sequence set forth in SEQ ID NO: 13; and a light chain variable region comprising a CDR1 consisting of the amino acid sequence set forth in SEQ ID NO: 14, a CDR2 consisting of the amino acid sequence set forth in SEQ ID NO: 15, and a CDR3 consisting of the amino acid sequence set forth in SEQ ID NO: 16; or
(b) a heavy chain variable region comprising a CDR1 consisting of the amino acid sequence set forth in SEQ ID NO: 17, a CDR2 consisting of the amino acid sequence set forth in SEQ ID NO: 18, and a CDR3 consisting of the amino acid sequence set forth in SEQ ID NO: 19; and a light chain variable region comprising a CDR1 consisting of the amino acid sequence set forth in SEQ ID NO: 20, a CDR2 consisting of the amino acid sequence set forth in SEQ ID NO: 21, and a CDR3 consisting of the amino acid sequence set forth in SEQ ID NO: 22.

2. An anti-canine PD-L1 antibody that specifically binds to a canine PD-L1 consisting of the amino acid sequence set forth in SEQ ID NO: 6,
said antibody comprising:
(a) a heavy chain variable region comprising a CDR1 consisting of the amino acid sequence set forth in SEQ ID NO: 23, a CDR2 consisting of the amino acid sequence set forth in SEQ ID NO: 24, and a CDR3 consisting of the amino acid sequence set forth in SEQ ID NO: 25; and a light chain variable region comprising a CDR1 consisting of the amino acid sequence set forth in SEQ ID NO: 26, a CDR2 consisting of the amino acid sequence set forth in SEQ ID NO: 27, and a CDR3 consisting of the amino acid sequence set forth in SEQ ID NO: 28; or
(b) a heavy chain variable region comprising a CDR1 consisting of the amino acid sequence set forth in SEQ ID NO: 29, a CDR2 consisting of the amino acid sequence set forth in SEQ ID NO: 30, and a CDR3 consisting of the amino acid sequence set forth in SEQ ID NO: 31; and a light chain variable region comprising a CDR1 consisting of the amino acid sequence set forth in SEQ ID NO: 32, a CDR2 consisting of the amino acid sequence set forth in SEQ ID NO: 33, and a CDR3 consisting of the amino acid sequence set forth in SEQ ID NO: 34.

3. A method for inhibiting binding between a canine PD-1 and a canine PD-L1 comprising using the antibody according to claim 1.

4. A gene encoding the antibody according to claim 1.

5. The anti-canine PD-1 antibody according to claim 1, wherein the anti-canine PD-1 antibody described in (a) is an anti-canine PD-1 antibody comprising:
(c) a heavy chain variable region comprising the amino acid sequence set forth in SEQ ID NO: 2 or an amino acid sequence having an identity of 90% or more with the amino acid sequence set forth in SEQ ID NO: 2; and a light chain variable region comprising the amino acid sequence set forth in SEQ ID NO: 3 or an amino acid sequence having an identity of 90% or more with the amino acid sequence set forth in SEQ ID NO: 3; and
the anti-canine PD-1 antibody described in (b) is an anti-canine PD-1 antibody comprising:
(d) a heavy chain variable region comprising the amino acid sequence set forth in SEQ ID NO: 4 or an amino acid sequence having an identity of 90% or more with the amino acid sequence set forth in SEQ ID NO: 4; and a light chain variable region comprising the amino acid sequence set forth in SEQ ID NO: 5 or an amino acid sequence having an identity of 90% or more with the amino acid sequence set forth in SEQ ID NO: 5.

6. The anti-canine PD-L1 antibody according to claim 2, wherein the anti-canine PD-L1 antibody described in (a) is an anti-canine PD-L1 antibody comprising:
(c) a heavy chain variable region comprising the amino acid sequence set forth in SEQ ID NO: 7 or an amino acid sequence having an identity of 90% or more with the amino acid sequence set forth in SEQ ID NO: 7; and a light chain variable region comprising the amino acid sequence set forth in SEQ ID NO: 8 or an amino acid sequence having an identity of 90% or more with the amino acid sequence set forth in SEQ ID NO: 8; and
the anti-canine PD-L1 antibody described in (b) is an anti-canine PD-L1 antibody comprising:
(d) a heavy chain variable region comprising the amino acid sequence set forth in SEQ ID NO: 9 or an amino acid sequence having an identity of 90% or more with the amino acid sequence set forth in SEQ ID NO: 9; and a light chain variable region comprising the amino acid sequence set forth in SEQ ID NO: 10 or an amino acid sequence having an identity of 90% or more with the amino acid sequence set forth in SEQ ID NO: 10.

7. A method for inhibiting binding between a canine PD-1 and a canine PD-L1 comprising using the antibody according to claim 2.

8. A method for inhibiting binding between a canine PD-1 and a canine PD-L1 comprising using the antibody according to claim 5.

9. A method for inhibiting binding between a canine PD-1 and a canine PD-L1 comprising using the antibody according to claim 6.

10. A gene encoding the antibody according to claim 2.

11. A gene encoding the antibody according to claim 5.

12. A gene encoding the antibody according to claim 6.

* * * * *